United States Patent
Jung et al.

(10) Patent No.: US 6,858,778 B1
(45) Date of Patent: Feb. 22, 2005

(54) PLANTS TRANSFORMED WITH A DNA CONSTRUCT COMPRISING A NUCLEIC ACID MOLECULE ENCODING AN 18 KD α-GLOBULIN

(75) Inventors: Rudolf Jung, Des Moines, IA (US); Wang-Nan Hu, Johnston, IA (US); Robert B. Meeley, Des Moines, IA (US); Vincent J. H. Sewalt, West Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 14 days.

(21) Appl. No.: 10/053,410

(22) Filed: Nov. 7, 2001

Related U.S. Application Data
(60) Provisional application No. 60/246,455, filed on Nov. 7, 2000.

(51) Int. Cl.[7] .................. C12N 15/11; C12N 15/29; C12N 15/82; A01H 5/00
(52) U.S. Cl. ............... 800/298; 800/287; 800/278; 800/290; 536/23.6; 536/24.1; 435/419
(58) Field of Search .................. 800/298, 287, 800/278, 290, 284, 320.1; 536/23.6, 24.1, 23.1; 435/419, 468, 320.1

(56) References Cited

U.S. PATENT DOCUMENTS
6,160,208 A    12/2000    Lundquist et al. ....... 800/320.1

FOREIGN PATENT DOCUMENTS
WO    WO 98/26064    6/1998    .......... C12N/15/11

OTHER PUBLICATIONS
Bowie et al (1990, Science 247:1306–10).*
McConnell et al (2001, Nature 411 (6838):709–713).*
Fourgoux–Nicol et al (1999, Plant Molecular Biology 40:857–872).*
Shorrosh et al (1999, NCBI Accession No. X63990).*
Singh et al (1997, Plant Science 130:189–196).*

* cited by examiner

*Primary Examiner*—Amy J. Nelson
*Assistant Examiner*—Stuart F. Baum
(74) *Attorney, Agent, or Firm*—Kathryn K. Lappegard; Pioneer Hi-Bred Int'l Inc.

(57) ABSTRACT

The present invention is directed to a composition for altering the levels of seed proteins in cereal grain. The invention is directed to the alteration of seed protein levels in plant grain, resulting in grain with increased digestibility/nutrient availability, improved amino acid composition/nutritional value, increased response to feed processing, improved silage quality, and increased efficiency of wet or dry-milling. The composition provided comprises a nucleotide sequence encoding a maize 18 kD alpha-globulin cDNA as well as expression cassettes comprising nucleotide sequences of the invention. Also provided are transformed plant tissue including plants, cells and seeds thereof.

11 Claims, No Drawings

SEQUENCE LISTING

```
<160> NUMBER OF SEQ ID NOS: 10

<210> SEQ ID NO 1
<211> LENGTH: 1129
<212> TYPE: DNA
<213> ORGANISM: Zea mays
<220> FEATURE:
<221> NAME/KEY: CDS
<222> LOCATION: (120)...(1004)
<223> OTHER INFORMATION: 50 kD gamma-zein prolamin/PTA 2272

<400> SEQUENCE: 1
gtgtatttgc actcatgcat cacaaaacat ccttctatca gtaccatcaa tcatcattca      60
tcttagtagt ataggcacca aatcaaatct gcaacatcaa ttatctaact ccaaaaacc      119 atg aag ctg gtg ctt gtg gtt ctt gct ttc att gct tta gta tca agt      167
Met Lys Leu Val Leu Val Val Leu Ala Phe Ile Ala Leu Val Ser Ser
 1               5                  10                  15 gtt tct tgt aca cag aca ggc ggc tgc agc tgt ggt caa caa caa agc      215
Val Ser Cys Thr Gln Thr Gly Gly Cys Ser Cys Gly Gln Gln Gln Ser
             20                  25                  30 cat gag cag caa cat cat cca caa caa cat cat cca caa aaa caa caa      263
His Glu Gln Gln His His Pro Gln Gln His His Pro Gln Lys Gln Gln
         35                  40                  45 cat caa cca cca cca caa cat cac cag cag cag caa cac caa caa caa      311
His Gln Pro Pro Pro Gln His His Gln Gln Gln Gln His Gln Gln Gln
     50                  55                  60 caa gtt cac atg caa cca caa aaa cat cag caa caa caa gaa gtt cat      359
Gln Val His Met Gln Pro Gln Lys His Gln Gln Gln Gln Glu Val His
 65                  70                  75                  80 gtt caa caa caa caa caa ccg cag cac caa caa caa caa caa caa caa      407
Val Gln Gln Gln Gln Gln Pro Gln His Gln Gln Gln Gln Gln Gln Gln
                 85                  90                  95 caa cag cac caa caa caa cat caa tgt gaa ggc caa caa caa cat cac      455
Gln Gln His Gln Gln Gln His Gln Cys Glu Gly Gln Gln Gln His His
            100                 105                 110 caa caa tca caa ggc cat gtg caa caa cac gaa cag agc cat gag caa      503
Gln Gln Ser Gln Gly His Val Gln Gln His Glu Gln Ser His Glu Gln
        115                 120                 125 cac caa gga cag agc cat gag caa caa cat caa caa caa ttc cag ggt      551
His Gln Gly Gln Ser His Glu Gln Gln His Gln Gln Gln Phe Gln Gly
    130                 135                 140 cat gac aag cag caa caa cca caa cag cct cag caa tat cag cag ggc      599
His Asp Lys Gln Gln Gln Pro Gln Gln Pro Gln Gln Tyr Gln Gln Gly
145                 150                 155                 160
```

-continued

| | |
|---|---|
| cag gaa aaa tca caa cag caa caa tgt cat tgc cag gag cag caa cag<br>Gln Glu Lys Ser Gln Gln Gln Gln Cys His Cys Gln Glu Gln Gln Gln<br>                      165                      170                      175 | 647 |
| act aca agg tgc agc tat aac tac tat agc agt agc tca aat cta aaa<br>Thr Thr Arg Cys Ser Tyr Asn Tyr Tyr Ser Ser Ser Ser Asn Leu Lys<br>                      180                      185                      190 | 695 |
| aat tgt cat gaa ttc cta agg cag cag tgc agc cct ttg gta atg cct<br>Asn Cys His Glu Phe Leu Arg Gln Gln Cys Ser Pro Leu Val Met Pro<br>            195                      200                      205 | 743 |
| ttt ctc caa tca cgt ttg ata caa cca agt agc tgc cag gta ttg cag<br>Phe Leu Gln Ser Arg Leu Ile Gln Pro Ser Ser Cys Gln Val Leu Gln<br>210                      215                      220 | 791 |
| caa caa tgt tgt cat gat ctt agg cag att gag cca caa tac att cac<br>Gln Gln Cys Cys His Asp Leu Arg Gln Ile Glu Pro Gln Tyr Ile His<br>225                      230                      235                      240 | 839 |
| caa gca atc tac aac atg gtt caa tcc ata atc cag gag gag caa caa<br>Gln Ala Ile Tyr Asn Met Val Gln Ser Ile Ile Gln Glu Glu Gln Gln<br>                      245                      250                      255 | 887 |
| caa caa cca tgt gag tta tgt gga tct caa caa gct act cca aag tgc<br>Gln Gln Pro Cys Glu Leu Cys Gly Ser Gln Gln Ala Thr Pro Lys Cys<br>            260                      265                      270 | 935 |
| ggt ggc aat ctt gac agc agc aca ata cct acc atc aat gtg cgg ctt<br>Gly Gly Asn Leu Asp Ser Ser Thr Ile Pro Thr Ile Asn Val Arg Leu<br>275                      280                      285 | 983 |
| gta cca ctc ata cta cca aaa taatccatgc agcagcaatg acattagtgg<br>Val Pro Leu Ile Leu Pro Lys<br>            290                      295 | 1034 |
| tgtttgcaat tgaagaattg tgtctaccta gccgttatac tcatataacg gtgttaagca | 1094 |
| ataaagtacc atacattatg atgttaaaaa aaaaa | 1129 |

<210> SEQ ID NO 2
<211> LENGTH: 295
<212> TYPE: PRT
<213> ORGANISM: Zea mays

<400> SEQUENCE: 2

Met Lys Leu Val Leu Val Val Leu Ala Phe Ile Ala Leu Val Ser Ser
  1               5                  10                  15

Val Ser Cys Thr Gln Thr Gly Gly Cys Ser Cys Gly Gln Gln Gln Ser
             20                  25                  30

His Glu Gln Gln His His Pro Gln Gln His His Pro Gln Lys Gln Gln
         35                  40                  45

His Gln Pro Pro Pro Gln His His Gln Gln Gln Gln His Gln Gln Gln
     50                  55                  60

Gln Val His Met Gln Pro Gln Lys His Gln Gln Gln Gln Glu Val His
 65                  70                  75                  80

Val Gln Gln Gln Gln Gln Pro Gln His Gln Gln Gln Gln Gln Gln Gln
                 85                  90                  95

Gln Gln His Gln Gln His Gln Cys Glu Gly Gln Gln His His
             100                 105                 110

Gln Gln Ser Gln Gly His Val Gln His Glu Gln Ser His Glu Gln
         115                 120                 125

His Gln Gly Gln Ser His Glu Gln Gln Gln Gln Phe Gln Gly
     130                 135                 140

His Asp Lys Gln Gln Gln Pro Gln Gln Pro Gln Gln Tyr Gln Gln Gly
145                 150                 155                 160

-continued

```
Gln Glu Lys Ser Gln Gln Gln Cys His Cys Gln Glu Gln Gln
            165                 170                 175

Thr Thr Arg Cys Ser Tyr Asn Tyr Tyr Ser Ser Ser Asn Leu Lys
            180                 185                 190

Asn Cys His Glu Phe Leu Arg Gln Gln Cys Ser Pro Leu Val Met Pro
            195                 200                 205

Phe Leu Gln Ser Arg Leu Ile Gln Pro Ser Ser Cys Gln Val Leu Gln
210                 215                 220

Gln Gln Cys Cys His Asp Leu Arg Gln Ile Glu Pro Gln Tyr Ile His
225                 230                 235                 240

Gln Ala Ile Tyr Asn Met Val Gln Ser Ile Ile Gln Glu Glu Gln Gln
                245                 250                 255

Gln Gln Pro Cys Glu Leu Cys Gly Ser Gln Gln Ala Thr Pro Lys Cys
            260                 265                 270

Gly Gly Asn Leu Asp Ser Ser Thr Ile Pro Thr Ile Asn Val Arg Leu
            275                 280                 285

Val Pro Leu Ile Leu Pro Lys
            290                 295

<210> SEQ ID NO 3
<211> LENGTH: 950
<212> TYPE: DNA
<213> ORGANISM: Zea mays
<220> FEATURE:
<221> NAME/KEY: CDS
<222> LOCATION: (111)...(728)
<223> OTHER INFORMATION: 18 kD alpha-globulin/PTA 2274

<400> SEQUENCE: 3
aaaaaaaccc cctcgtcgat caccaccaaa gaacacagta actagcagct agcacatcaa    60
acaagtggcg acagacaaag atttgtgagg gtgatccgcg ctgagaagag atg gct     116
                                                        Met Ala
                                                          1 aag atc gcc gcg gcg gcg gcg gcg gcg ctg tgc ttc gcg gcc ctg gtg    164
Lys Ile Ala Ala Ala Ala Ala Ala Ala Leu Cys Phe Ala Ala Leu Val
        5                   10                  15 gcc gtg gcc gtc tgc caa ggc gag gtc gag cgg cag agg ctc agg gac    212
Ala Val Ala Val Cys Gln Gly Glu Val Glu Arg Gln Arg Leu Arg Asp
    20                  25                  30 ctg cag tgc tgg cag gag gtc cag gag agc ccg ctc gac gcg tgc cgc    260
Leu Gln Cys Trp Gln Glu Val Gln Glu Ser Pro Leu Asp Ala Cys Arg
35                  40                  45                  50 cag gtc ctc gac cgg cag cta acc ggc ggc ggc ggc ggc ggc gtt       308
Gln Val Leu Asp Arg Gln Leu Thr Gly Gly Gly Gly Gly Gly Val
                55                  60                  65 ggc ccg ttc cgg tgg ggc acc ggg ctc cgg atg cgg tgc tgc cag cag    356
Gly Pro Phe Arg Trp Gly Thr Gly Leu Arg Met Arg Cys Cys Gln Gln
            70                  75                  80 ctc cag gac gtg agc cgc gag tgc cgc tgc gcc gcc atc cgg agc atg    404
Leu Gln Asp Val Ser Arg Glu Cys Arg Cys Ala Ala Ile Arg Ser Met
        85                  90                  95 gtc agg ggc tac gag gag gcc atg ccg ccg ctg gag aaa ggc tgg tgg    452
Val Arg Gly Tyr Glu Glu Ala Met Pro Pro Leu Glu Lys Gly Trp Trp
    100                 105                 110 cca tgg ggg cgg cag cag cag ccg ccg ccg cag gga gga gga gga gga    500
Pro Trp Gly Arg Gln Gln Gln Pro Pro Pro Gln Gly Gly Gly Gly Gly
115                 120                 125                 130 cag ggg ggc tac tac tac ccc tgc agc cgg cca gga gag gga tac ggc    548
Gln Gly Gly Tyr Tyr Tyr Pro Cys Ser Arg Pro Gly Glu Gly Tyr Gly
```

```
                    135                 140                 145
tac ggt cag ggt ggc cag cgg cag atg tat cca ccg tgt cgt ccc ggc       596
Tyr Gly Gln Gly Gly Gln Arg Gln Met Tyr Pro Pro Cys Arg Pro Gly
            150                 155                 160 acc acc ggc ggc ggg cca agg atc ggc cgc gtg agg ctt acg aag gcc       644
Thr Thr Gly Gly Gly Pro Arg Ile Gly Arg Val Arg Leu Thr Lys Ala
        165                 170                 175 cgg gag tac gcc gcg ggg ttg ccg atg atg tgc cgg ctg tcg gag ccc       692
Arg Glu Tyr Ala Ala Gly Leu Pro Met Met Cys Arg Leu Ser Glu Pro
    180                 185                 190 cag gag tgc agc atc ttc tcc ggc ggc gac cag tac tagctaccat            738
Gln Glu Cys Ser Ile Phe Ser Gly Gly Asp Gln Tyr
195                 200                 205 ggttaaagcg agtcggcgcg aggtgcaaga cgcagcatgt gtactgtgcg cgtgcaaatc     798
cagaatgacg tagctctgac gtgggctcgc aatattgtcg cgtgttcgtt acaataatga     858
taataactat gaggaataaa tatgggaatg ttgccagata gtactggcgc cggttcttca     918
aaaaaaaaaa aaaaaaaaaa aaaaaaaaaa aa                                   950

<210> SEQ ID NO 4
<211> LENGTH: 206
<212> TYPE: PRT
<213> ORGANISM: Zea mays

<400> SEQUENCE: 4

Met Ala Lys Ile Ala Ala Ala Ala Ala Ala Leu Cys Phe Ala Ala
 1               5                  10                  15

Leu Val Ala Val Ala Val Cys Gln Gly Glu Val Glu Arg Gln Arg Leu
                20                  25                  30

Arg Asp Leu Gln Cys Trp Gln Glu Val Gln Glu Ser Pro Leu Asp Ala
            35                  40                  45

Cys Arg Gln Val Leu Asp Arg Gln Leu Thr Gly Gly Gly Gly Gly
        50                  55                  60

Gly Val Gly Pro Phe Arg Trp Gly Thr Gly Leu Arg Met Arg Cys Cys
 65                 70                  75                  80

Gln Gln Leu Gln Asp Val Ser Arg Glu Cys Arg Cys Ala Ala Ile Arg
                85                  90                  95

Ser Met Val Arg Gly Tyr Glu Glu Ala Met Pro Pro Leu Glu Lys Gly
            100                 105                 110

Trp Trp Pro Trp Gly Arg Gln Gln Pro Pro Gln Gly Gly Gly
        115                 120                 125

Gly Gly Gln Gly Gly Tyr Tyr Tyr Pro Cys Ser Arg Pro Gly Glu Gly
    130                 135                 140

Tyr Gly Tyr Gly Gln Gly Gly Gln Arg Gln Met Tyr Pro Pro Cys Arg
145                 150                 155                 160

Pro Gly Thr Thr Gly Gly Gly Pro Arg Ile Gly Arg Val Arg Leu Thr
                165                 170                 175

Lys Ala Arg Glu Tyr Ala Ala Gly Leu Pro Met Met Cys Arg Leu Ser
            180                 185                 190

Glu Pro Gln Glu Cys Ser Ile Phe Ser Gly Gly Asp Gln Tyr
        195                 200                 205

<210> SEQ ID NO 5
<211> LENGTH: 1679
<212> TYPE: DNA
<213> ORGANISM: Zea mays
<220> FEATURE:
```

<221> NAME/KEY: CDS
<222> LOCATION: (34)...(1485)
<223> OTHER INFORMATION: 50 kD legumin-1 prolamin/PTA 2273

<400> SEQUENCE: 5

```
gcacgaggag cgagcgagca gaggcagcgc aca atg gcg gcg gca ata gta ctc        54
                                    Met Ala Ala Ala Ile Val Leu
                                      1               5 tcc ggc cag gtg cgg ccg ctt ccc tcg tcg ctg ccc ctg tcc ctg ctg       102
Ser Gly Gln Val Arg Pro Leu Pro Ser Ser Leu Pro Leu Ser Leu Leu
         10                  15                  20 ctg ctc ctc ctc ctg tgc tgc tcc ggc acc tcg tgg gga tgg agc acg       150
Leu Leu Leu Leu Leu Cys Cys Ser Gly Thr Ser Trp Gly Trp Ser Thr
     25                  30                  35 tcc cgg gga gga gcc gcc agg gag tgc ggc ttc gat ggc aag ctg gag       198
Ser Arg Gly Gly Ala Ala Arg Glu Cys Gly Phe Asp Gly Lys Leu Glu
 40                  45                  50                  55 gcc ctg gag ccg cgc cac aag gtg cag tct gag gcc ggc tcc gtc cag       246
Ala Leu Glu Pro Arg His Lys Val Gln Ser Glu Ala Gly Ser Val Gln
                 60                  65                  70 tac ttc agc cgg ttc aac gaa gcc gac cgg gag ctc acc tgc gcc ggc       294
Tyr Phe Ser Arg Phe Asn Glu Ala Asp Arg Glu Leu Thr Cys Ala Gly
             75                  80                  85 atc ttc gcc gtc cgc gtc gtc gtc gac gcc atg ggc ctc ctc ctc cct       342
Ile Phe Ala Val Arg Val Val Val Asp Ala Met Gly Leu Leu Leu Pro
         90                  95                 100 cga tac tcc aac gtc cat tcg ctt gtc tac atc gtc caa ggg aga ggg       390
Arg Tyr Ser Asn Val His Ser Leu Val Tyr Ile Val Gln Gly Arg Gly
     105                 110                 115 atc att ggg ttc tcg ttt ccg gga tgc caa gag gag acc cag cag cag       438
Ile Ile Gly Phe Ser Phe Pro Gly Cys Gln Glu Glu Thr Gln Gln Gln
120                 125                 130                 135 cag tat gga tac gga tat gga tat gga cac cat cac cag cat gac            486
Gln Tyr Gly Tyr Gly Tyr Gly Tyr Gly His His His Gln His Asp
                 140                 145                 150 cac cac aag atc cac cga ttc gag cag ggc gac gtg gtg gcc atg ccg       534
His His Lys Ile His Arg Phe Glu Gln Gly Asp Val Val Ala Met Pro
             155                 160                 165 gcc ggc gcc cag cac tgg ctg tac aac gac ggc gac gcg ccg ctt gtg       582
Ala Gly Ala Gln His Trp Leu Tyr Asn Asp Gly Asp Ala Pro Leu Val
         170                 175                 180 gcg gtc tac gtc ttc gac gag aac aac aac atc aac cag ctc gag cct       630
Ala Val Tyr Val Phe Asp Glu Asn Asn Asn Ile Asn Gln Leu Glu Pro
     185                 190                 195 tcc atg agg aaa ttt ttg ctg gct ggg ggc ttc agc aag ggg cag ccc       678
Ser Met Arg Lys Phe Leu Leu Ala Gly Gly Phe Ser Lys Gly Gln Pro
200                 205                 210                 215 cac ttc gcc gag aac atc ttc aaa ggg atc gac gcc cgg ttc ctg agc       726
His Phe Ala Glu Asn Ile Phe Lys Gly Ile Asp Ala Arg Phe Leu Ser
                 220                 225                 230 gaa gcc ctg ggc gtc agc atg cac gtc gcc gag aag ctg cag agc cgg       774
Glu Ala Leu Gly Val Ser Met His Val Ala Glu Lys Leu Gln Ser Arg
             235                 240                 245 cgt gac cag cga ggc gag atc gtc cgc gtg gag ccg gag cac ggc ttt       822
Arg Asp Gln Arg Gly Glu Ile Val Arg Val Glu Pro Glu His Gly Phe
         250                 255                 260 cac cag ctg aat ccg tcg ccg tcg tcg tcg ttt tcg ttc cca tcg           870
His Gln Leu Asn Pro Ser Pro Ser Ser Ser Phe Ser Phe Pro Ser
     265                 270                 275 tca caa gtc cag tac caa acg tgc cag cgc gac gtc gac agg cac aac       918
Ser Gln Val Gln Tyr Gln Thr Cys Gln Arg Asp Val Asp Arg His Asn
```

```
Ser Gln Val Gln Tyr Gln Thr Cys Gln Arg Asp Val Asp Arg His Asn
280                 285                 290                 295 gtc tgc gcc atg gag gtg agg cac agc gtc gaa cgg ctg gac cag gcc        966
Val Cys Ala Met Glu Val Arg His Ser Val Glu Arg Leu Asp Gln Ala
                        300                 305                 310 gac gtc tac agc cct ggg gct ggg agg atc aca cgc ctc acc agc cac       1014
Asp Val Tyr Ser Pro Gly Ala Gly Arg Ile Thr Arg Leu Thr Ser His
                315                 320                 325 aag ttc ccc gtc ctc aac ctc gta cag atg agc gcg gtg cgg gta gac       1062
Lys Phe Pro Val Leu Asn Leu Val Gln Met Ser Ala Val Arg Val Asp
        330                 335                 340 ctg tac cag gac gcc atc atg tcg ccg ttc tgg aac ttc aac gcc cac       1110
Leu Tyr Gln Asp Ala Ile Met Ser Pro Phe Trp Asn Phe Asn Ala His
345                 350                 355 agc gcc atg tac ggc atc agg ggc agt gca agg gtc cag gtc gcc agc       1158
Ser Ala Met Tyr Gly Ile Arg Gly Ser Ala Arg Val Gln Val Ala Ser
360                 365                 370                 375 gac aac ggg acc acg gtg ttc gac gac gtg ctc cgt gcg ggg cag ctg       1206
Asp Asn Gly Thr Thr Val Phe Asp Asp Val Leu Arg Ala Gly Gln Leu
                380                 385                 390 ctc atc gta ccc cag ggc tac ctc gtc gcc acc aag gcg cag gga gaa       1254
Leu Ile Val Pro Gln Gly Tyr Leu Val Ala Thr Lys Ala Gln Gly Glu
                395                 400                 405 ggc ttc cag tac atc gcc ttc gag acg aac cct gac acc atg gtc agc       1302
Gly Phe Gln Tyr Ile Ala Phe Glu Thr Asn Pro Asp Thr Met Val Ser
        410                 415                 420 cac gtc gcc ggg aag aac tcc gtc ctg agc gac ttg ccg gcc gcc gtc       1350
His Val Ala Gly Lys Asn Ser Val Leu Ser Asp Leu Pro Ala Ala Val
425                 430                 435 atc gcc agc tcg tat gcc atc tcc atg gag gaa gct gca gag ctc aag       1398
Ile Ala Ser Ser Tyr Ala Ile Ser Met Glu Glu Ala Ala Glu Leu Lys
440                 445                 450                 455 aac ggt agg aag cat gag ctg gct gtg ctt act cct gct ggc agt ggc       1446
Asn Gly Arg Lys His Glu Leu Ala Val Leu Thr Pro Ala Gly Ser Gly
                460                 465                 470 agc tac caa caa ggt caa gct ggc agc gcc caa cag tag gcacaacctc       1495
Ser Tyr Gln Gln Gly Gln Ala Gly Ser Ala Gln Gln *
                475                 480 agagtgatct gcctgaataa gtactcgtag actgtaataa ttaaacaaag cttgctcatg       1555
gttaaactgc gtgttgatta gtctttcaac tacatagctc taaagttttt gatacaccga       1615
gtgatttgcc aggaaaaaaa tgagcagatt gttgtaagca aaaaaaaaaa aaaaaaaaa       1675 aaaa                                                                    1679

<210> SEQ ID NO 6
<211> LENGTH: 483
<212> TYPE: PRT
<213> ORGANISM: Zea mays

<400> SEQUENCE: 6

Met Ala Ala Ala Ile Val Leu Ser Gly Gln Val Arg Pro Leu Pro Ser
1               5                   10                  15

Ser Leu Pro Leu Ser Leu Leu Leu Leu Leu Leu Cys Cys Ser Gly
            20                  25                  30

Thr Ser Trp Gly Trp Ser Thr Ser Arg Gly Gly Ala Ala Arg Glu Cys
        35                  40                  45

Gly Phe Asp Gly Lys Leu Glu Ala Leu Glu Pro Arg His Lys Val Gln
    50                  55                  60
```

```
Ser Glu Ala Gly Ser Val Gln Tyr Phe Ser Arg Phe Asn Glu Ala Asp
 65                  70                  75                  80

Arg Glu Leu Thr Cys Ala Gly Ile Phe Ala Val Arg Val Val Val Asp
                 85                  90                  95

Ala Met Gly Leu Leu Pro Arg Tyr Ser Asn Val His Ser Leu Val
                100                 105                 110

Tyr Ile Val Gln Gly Arg Gly Ile Ile Gly Phe Ser Phe Pro Gly Cys
                115                 120                 125

Gln Glu Glu Thr Gln Gln Gln Tyr Gly Tyr Gly Tyr Gly Tyr Gly
            130                 135                 140

His His His His Gln His Asp His Lys Ile His Arg Phe Glu Gln
145                 150                 155                 160

Gly Asp Val Val Ala Met Pro Ala Gly Ala Gln His Trp Leu Tyr Asn
                165                 170                 175

Asp Gly Asp Ala Pro Leu Val Ala Val Tyr Val Phe Asp Glu Asn Asn
            180                 185                 190

Asn Ile Asn Gln Leu Glu Pro Ser Met Arg Lys Phe Leu Leu Ala Gly
            195                 200                 205

Gly Phe Ser Lys Gly Gln Pro His Phe Ala Glu Asn Ile Phe Lys Gly
        210                 215                 220

Ile Asp Ala Arg Phe Leu Ser Glu Ala Leu Gly Val Ser Met His Val
225                 230                 235                 240

Ala Glu Lys Leu Gln Ser Arg Arg Asp Gln Arg Gly Glu Ile Val Arg
                245                 250                 255

Val Glu Pro Glu His Gly Phe His Gln Leu Asn Pro Ser Pro Ser Ser
                260                 265                 270

Ser Ser Phe Ser Phe Pro Ser Ser Gln Val Gln Tyr Gln Thr Cys Gln
        275                 280                 285

Arg Asp Val Asp Arg His Asn Val Cys Ala Met Glu Val Arg His Ser
    290                 295                 300

Val Glu Arg Leu Asp Gln Ala Asp Val Tyr Ser Pro Gly Ala Gly Arg
305                 310                 315                 320

Ile Thr Arg Leu Thr Ser His Lys Phe Pro Val Leu Asn Leu Val Gln
                325                 330                 335

Met Ser Ala Val Arg Val Asp Leu Tyr Gln Asp Ala Ile Met Ser Pro
            340                 345                 350

Phe Trp Asn Phe Asn Ala His Ser Ala Met Tyr Gly Ile Arg Gly Ser
        355                 360                 365

Ala Arg Val Gln Val Ala Ser Asp Asn Gly Thr Thr Val Phe Asp Asp
    370                 375                 380

Val Leu Arg Ala Gly Gln Leu Leu Ile Val Pro Gln Gly Tyr Leu Val
385                 390                 395                 400

Ala Thr Lys Ala Gln Gly Glu Gly Phe Gln Tyr Ile Ala Phe Glu Thr
                405                 410                 415

Asn Pro Asp Thr Met Val Ser His Val Ala Gly Lys Asn Ser Val Leu
            420                 425                 430

Ser Asp Leu Pro Ala Ala Val Ile Ala Ser Ser Tyr Ala Ile Ser Met
        435                 440                 445

Glu Glu Ala Ala Glu Leu Lys Asn Gly Arg Lys His Glu Leu Ala Val
    450                 455                 460

Leu Thr Pro Ala Gly Ser Gly Ser Tyr Gln Gln Gly Gln Ala Gly Ser
465                 470                 475                 480

Ala Gln Gln
```

<210> SEQ ID NO 7
<211> LENGTH: 324
<212> TYPE: DNA
<213> ORGANISM: Zea mays
<220> FEATURE:
<221> NAME/KEY: allele
<222> LOCATION: (0)...(0)
<223> OTHER INFORMATION: 50kD gamma-zein, B73 partial

<400> SEQUENCE: 7

```
ccagcagcag caacaccaac aacaacaagt tcacatgcaa ccacaaaaac atcagcaaca      60
acaagaagtt catgttcaac aacaacaaca acaaccgcag caccaacaac aacaacaaca     120
acaacagcac caacaacaac atcaatgtga aggccaacaa caacatcacc aacaatcaca     180
aggccatgtg caacaacacg aacagagcca tgagcaacac caaggacaga gccatgagca     240
acaacatcaa caacaattcc agggtcatga caagcagcaa caaccacaac agcctcagca     300
atatcagcag ggccaggaaa aatc                                            324
```

<210> SEQ ID NO 8
<211> LENGTH: 321
<212> TYPE: DNA
<213> ORGANISM: Zea mays
<220> FEATURE:
<221> NAME/KEY: allele
<222> LOCATION: (0)...(0)
<223> OTHER INFORMATION: 50kD gamma-zein, Mo17 partial

<400> SEQUENCE: 8

```
ccagcagcag caacaccaac aacaacaagt tcacatgcaa ccacaaaaac atcagcaaca      60
acaagaagtt catgttcaac aacaacaaca acaaccgcag caccaacaac aacaacaaca     120
acagcaccaa caacaacatc aatgtgaagg ccaacaacaa catcaccaac aatcacaagg     180
ccatgtgcaa caacacgaac agagccatga gcaacaccag gacagagcc atgagcaaca     240
acatcaacaa caattccagg gtcatgacaa gcagcaacaa ccacaacagc ctcagcaata     300
tcagcagggc caggaaaaat c                                               321
```

<210> SEQ ID NO 9
<211> LENGTH: 561
<212> TYPE: DNA
<213> ORGANISM: Zea mays
<220> FEATURE:
<221> NAME/KEY: allele
<222> LOCATION: (0)...(0)
<223> OTHER INFORMATION: 18 kD alpha-globulin, B73, partial

<400> SEQUENCE: 9

```
aattcgccct tgtcattctg gatttgcacg cgcacagtac acatgctgcg tcttgcacgt      60
cgcgccgact cgctttaacc atggtagcta gtactggtcg ccgccggaga agatgctgca     120
ctcctggggc tccgacagcc ggcacatcat cggcaacccc gcggcgtact cccgggcctt     180
cgtaagcctc acgcggccga tccttggccc gcgccggtg gtgccgggac gacacggtgg     240
atacatctgc cgctggccac cctgaccgta gccgtatccc tctcctggcc ggctgcaggg     300
gtagtagtag ccccccctgtc ctcctcctcc tccctgcggc ggcggctgct gctgccgccc    360
ccatggccac cagcctttct ccagcggcgg catggcctcc tcgtagcccc tgaccatgct     420
ccggatggcg gcgcagcggc actcgcggct cacgtcctgg agctgctggc agcaccgcat    480
ccggagcccg gtgcccacc ggaacgggcc aacgccgccg ccgccgccgc cgccggttag     540
```

```
                                                        -continued
ctgccggtcg aggaaagggc g                                                    561

<210> SEQ ID NO 10
<211> LENGTH: 537
<212> TYPE: DNA
<213> ORGANISM: Zea mays
<220> FEATURE:
<221> NAME/KEY: allele
<222> LOCATION: (0)...(0)
<223> OTHER INFORMATION: 18 kD alpha-globulin, Mo17 partial

<400> SEQUENCE: 10
aattcgccct tgtcattctg gatttgcacg cgcacagtac acatgctgcg ccttgcacgt           60
cgcgccgact cactcttttt tttttaaccc tggtagctag tactggtcgc cgccggagaa         120
gatgctgcac tcctggggct ccgacagccg gcacatcatc ggcaaccccg cggcgtactc         180
ccgggccttc gtaagcctca cgcggccgat ccttggcccg gtggtgccgg gacgacacgg         240
tggatacatc tgcgtttggt atccctctcc tgcccggctg cagggtagt agtagccccc          300 ctgtcctcct cctcctccct gcggcggcgg ctgctgctgc cgcccccatg gccaccagcc         360
tttctccaga ggcggcatgg cctcctcgta gcccctgacc atgctccgga tggcggcgca         420
gcggcactcg cggctcacgt cctggagctg ctggcagcac cgcatccgga gcccggtgcc         480
ccaccggaac gggccgccga cgccgccgcc ggttagctgc cggtcgagga aagggcg            537
```

PLANTS TRANSFORMED WITH A DNA CONSTRUCT COMPRISING A NUCLEIC ACID MOLECULE ENCODING AN 18 KD α-GLOBULIN

CROSS REFERENCE TO RELATED APPLICATIONS

This application claims the benefit of U.S. application Ser. No. 60/246,455, filed Nov. 7, 2000, which is herein incorporated by reference.

FIELD OF THE INVENTION

The invention relates to the field of plant molecular biology and the use of genetic modification to improve the quality of crop plants, more particularly to methods for improving the nutritional value of grain and the efficiency of grain processing.

DETAILED DESCRIPTION OF THE INVENTION

The present invention is directed to compositions and methods for altering the levels of seed proteins in plant seed, particularly reducing the levels of gamma-zein proteins in maize and the levels of gamma-kafarin in sorghum. Modification of seed protein composition causes changes in the physical and/or chemical properties of the grain.

The invention is directed to the alteration of protein levels in plant seed, resulting in grain with increased digestibility/nutrient availability, improved amino acid composition/nutrient value, increased response to feed processing, improved silage quality, increased efficiency of wet or dry milling, and decreased allergenicity and/or toxicity. The claimed sequences encode proteins preferentially expressed during seed development.

As used herein, "grain" means the mature seed produced by commercial growers for purposes other than growing or reproducing the species.

Additional uses of the invention include increasing seed hardness, decreasing seed caloric value for use in diet foods and other food for human use, pet food, increasing the antioxidant properties of seed, and taking advantage of the metal chelating properties of the legumin 1 protein of the invention to purify other polypeptides of interest.

Compositions of the invention comprise sequences encoding maize seed proteins and variants and fragments thereof. Methods of the invention involve the use of transgenic expression, antisense suppression, co-suppression, mutagenesis including transposon tagging, and biosynthetic competition to manipulate, in plants and plant seeds and grains, the expression of seed proteins, including, but not limited to, those encoded by the sequences disclosed herein. Transgenic plants producing seeds and grain with altered seed protein content are also provided. The modified seed and grain of the invention may be obtained by breeding crosses with the transgenic plants, such as by marker assisted selected breeding. The 50 kD gamma-zein of the instant invention maps to chromosome 7, bin 7.03, the 18 kD alpha-globulin to chromosome 6, bin 6.05, and the 50 kD legumin 1 to chromosome 6, Bin 6.01. This information enables one of skill in the art to employ these map locations to generate improved maize lines with altered seed protein levels.

It is recognized that while the invention is exemplified by the modulation of expression of selective sequences in maize, similar methods can be used to modulate the levels of seed proteins in other plants, particularly other cereals such as sorghum. In this manner, the sequences of the invention can be used to identify and isolate similar sequences in other plants based on sequence homology or sequence identity. Alternatively, where the maize sequences share sufficient homology to modulate expression of the native genes, such as in sorghum, the maize sequences may be used to modulate expression in sorghum. For a review of sorghum seed proteins including gamma-kafarin see Leite et al., *The Prolamins of Sorghum, Coix and Millets.*, In: Shewry and Casey (eds.) (1999) *Seed Proteins,* 141–157, Academic Publishers, Dordrecht.

In particular, the present invention provides isolated nucleic acid molecules comprising a nucleotide sequence encoding a maize protein, designated herein as the 50 kD gamma-zein, having the amino acid sequence shown in SEQ ID NO:2, or the nucleotide sequence encoding the DNA sequence deposited in a bacterial host as Patent Deposit No. PTA-2272. Further provided is a polypeptide having an amino acid sequence encoded by the nucleic acid molecules described herein, for example that set forth in SEQ ID NO:1, and deposited in a bacterial host as Patent Deposit No. PTA-2272, and fragments and variants thereof.

The present invention also provides isolated nucleic acid molecules comprising a nucleotide sequence encoding a maize protein, herein designated as the 18 kD alpha-globulin, having the amino acid sequence shown in SEQ ID NO:4, or the nucleotide sequence encoding the DNA sequence deposited in a bacterial host as Patent Deposit No. PTA-2274. Further provided is a polypeptide having an amino acid sequence encoded by the nucleic acid molecules described herein, for example that set forth in SEQ ID NO:3, and deposited in a bacterial host as Patent Deposit No. PTA-2274, and fragments and variants thereof.

The present invention also provides isolated nucleic acid molecules comprising a nucleotide sequence encoding a maize protein, herein designated as the 50 kD legumin 1 prolamin, having the amino acid sequence shown in SEQ ID NO:6, or the nucleotide sequence encoding the DNA sequence deposited in a bacterial host as Patent Deposit No. PTA-2273. Further provided is a polypeptide having an amino acid sequence encoded by the nucleic acid molecules described herein, for example that set forth in SEQ ID NO:5, and deposited in a bacterial host as Patent Deposit No. PTA-2273, and fragments and variants thereof.

A plasmid containing the nucleotide sequence encoding the 50 kD gamma-zein protein was deposited with the Patent Depository of the American Type Culture Collection (ATCC), Manassas, Va., on Jul. 26, 2000 and assigned Patent Deposit No. PTA-2272. A plasmid containing the nucleotide sequence encoding the 18 kD alpha-globulin protein was deposited with the Patent Depository of the American Type Culture Collection (ATCC), Manassas, Va., on Jul. 26, 2000 and assigned Patent Deposit No. PTA-2274. A plasmid containing the nucleotide sequence encoding the 50 kD legumin 1 protein was deposited with the Patent Depository of the American Type Culture Collection (ATCC), Manassas, Va., on Jul. 26, 2000 and assigned Patent Deposit No. PTA-2273. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

A comparison of the amino acid content of cereal grains shows that 18 kD alpha-globulin is an excellent source of tryptophan and methionine for amino acid balance in all cereals and that 50 kD legumin 1 prolamin is an excellent source of methionine for all cereals and a good source of lysine and tryptophan for the amino acid balance of most cereals.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native 50 kD gamma-zein, the 18 kD alpha-globulin, or the 50 kD legumin 1 proteins. Alternatively, fragments of a nucleotide sequence that are useful as hybridization probes generally do not encode fragment proteins retaining biological activity. Thus, fragments of a nucleotide sequence may range from at least about 40 nucleotides, about 50 nucleotides, about 100 nucleotides, and up to the full-length nucleotide sequence encoding the native 50 kD gamma-zein, the 18 kD alpha-globulin, or the 50 kD legumin 1 protein of the invention.

Fragments of the maize nucleotide sequences of the invention (SEQ ID NO:1, SEQ ID NO:3, or SEQ ID NO:5) that encode a biologically active portion of the 50 kD gamma-zein protein, the 18 kD alpha-globulin protein, or the 50 kD legumin 1 protein of the invention, respectively, will encode at least 15, 25, 30, 50, 100, 150, or 200 contiguous amino acids, or up to the total number of amino acids present in the full-length 50 kD gamma-zein protein, the 18 kD alpha-globulin protein, or the 50 kD legumin 1 protein of the invention (for example, 295 amino acids for SEQ ID NO:1; 206 amino acids for SEQ ID NO:3; and 483 amino acids for SEQ ID NO:5). Fragments of SEQ ID NO:1, SEQ ID NO:3, and SEQ ID NO:5 that are useful as hybridization probes or PCR primers need not encode a biologically active portion of a prolamin protein.

Thus, a fragment of SEQ ID NO:1, SEQ ID NO:3, or SEQ ID NO:5 may encode a biologically active portion of a prolamin protein, or it may be a fragment that can be used as a hybridization probe or PCR primer using methods disclosed below. A biologically active portion of the 50 kD gamma-zein protein, the 18 kD alpha-globulin protein, or the 50 kD legumin 1 protein of the invention can be prepared by isolating a portion of the disclosed nucleotide sequence that codes for a portion of the 50 kD gamma-zein protein, the 18 kD alpha-globulin protein, or the 50 kD legumin 1 protein (e.g., by recombinant expression in vitro), and assessing the activity of the encoded portion of the prolamin protein. Nucleic acid molecules that are fragments of SEQ ID NO:1 comprise at least 40, 50, 75, 100, 150, 200, 250, 300, 350, 400, 450, 500, 550, 600, 650, 700, 800, 900, 1000, or 1100 nucleotides, or up to the number of nucleotides present in the full-length gamma-zein cDNA (for example, 1129 nucleotides for SEQ ID NO:1). Nucleic acid molecules that are fragments of SEQ ID NO:3 comprise at least 40, 50, 75, 100, 150, 200, 250, 300, 350, 400, 450, 500, 550, 600, 650, 700, 800, or 900 nucleotides, or up to the number of nucleotides present in the full-length alpha-globulin cDNA (for example, 950 nucleotides for SEQ ID NO:3). Nucleic acid molecules that are fragments of SEQ ID NO:5 comprise at least 40, 50, 75, 100, 150, 200, 250, 300, 350, 400, 450, 500, 550, 600, 650, 700, 800, 1000, 1200, 1400, or 1600 nucleotides, or up to the number of nucleotides present in the full-length legumin 1 prolamin cDNA (for example, 1679 nucleotides for SEQ ID NO:5).

By "variants" is intended substantially similar sequences. For nucleotide sequences, conservative variants include those sequences that, because of the degeneracy of the genetic code, encode the amino acid sequence of 50 kD gamma-zein protein, the 18 kD alpha-globulin protein, or the 50 kD legumin 1 protein of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a 50 kD gamma-zein protein, an 18 kD alpha-globulin protein, or an 50 kD legumin 1 protein. Generally, variants of a particular nucleotide sequence of the invention will have at least about 60%, 65%, 70%, 75%, 80%, 85%, 90%, 91%, 92%, 93%, 94%, 95%, 96%, 97%, 98%, or 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the activity of the native prolamin proteins of the invention as described herein. Such variants may result from, for example, genetic polymorphism or from human manipulation. Biologically active variants of the native 50 kD gamma-zein protein, the 18 kD alpha-globulin protein, or the 50 kD legumin 1 protein of the invention will have at least about 60%, 65%, 70%, 75%, 80%, 85%, 90%, 91%, 92%, 93%, 94%, 95%, 96%, 97%, 98%, or 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the 50 kD gamma-zein protein, the 18 kD alpha-globulin protein, or the 50 kD legumin 1 protein can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference.

Thus, the genes and nucleotide sequences of the invention include both the naturally occurring sequences as well as mutant forms. Likewise, the proteins of the invention encompass both naturally occurring variant proteins as well as variations and modified forms thereof. Such variants will continue to possess the native seed protein activity. Obviously, the mutations that will be made in the DNA encoding the variant must not place the sequence out of reading frame and preferably will not create complementary regions that could produce secondary mRNA structure. See EP Patent Application Publication No. 75,444.

Variant nucleotide sequences and proteins also encompass sequences and proteins derived from a mutagenic and recombinogenic procedure such as DNA shuffling. With such a procedure, one or more different gamma-zein, alpha-globulin, or legumin protein coding sequences can be manipulated to create a new gamma-zein, alpha-globulin, or legumin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between 50 kD gamma-zein coding sequence, the 18 kD alpha-globulin coding sequence, or the 50 kD legumin 1 prolamin coding sequence of the invention and other known gene coding sequences to obtain a new coding sequence for a protein with an improved property of interest. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:45044509; Crameri et al. (1998) *Nature* 391:288–291; and U.S. Pat. Nos. 5,605,793 and 5,837,458.

The nucleotide sequence of the invention can be used to isolate corresponding sequences from other plants. In this manner, methods such as PCR, hybridization, and the like can be used to identify such sequences based on their sequence homology to the sequence set forth herein. Sequences isolated based on their sequence identity to the entire 50 kD gamma-zein, 18 kD alpha-globulin, or 50 kD legumin 1 sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on, for example, the 50 kD gamma zein sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire 50 kD gamma-zein, 18 kD alpha-globulin, or 50 kD legumin 1 sequence disclosed herein, or one or more portions thereof, may be used as a probe capable of specifically hybridizing to corresponding seed protein sequences and messenger RNAs. To achieve specific hybridization under a variety of conditions, such probes include sequences that are unique among the seed protein sequences of the invention and are preferably at least about 40 nucleotides in length. Such probes may be used to amplify corresponding gamma-zein, alpha-globulin, and legumin 1 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al.(1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode polypeptides that function as a seed protein and which hybridize under stringent conditions to the 50 kD gamma-zein, the 18 kD alpha-globulin protein, or the 50 kD legumin 1 sequence disclosed herein, or to fragments thereof, are encompassed by the present invention. Such sequences will be at least about 60%, 65%, 70%, 75%, 80%, 85%, 90%, 91%, 92%, 93%, 94%, 95%, 96%, 97%, 98%, or 99% or more homologous with the disclosed sequence. That is, the sequence identity of sequences may range, sharing at least about 60%, 65%, 70%, 75%, 80%, 85%, 90%, 91%, 92%, 93%, 94%, 95%, 96%, 97%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA).

Alignments using these programs can be performed using the default parameters. The CLUSTAL program is well described by Higgins et al.(1988) *Gene* 73:237–244 (1988); Higgins et al. (1989)*CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http:///www.ncbi.nim.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program, aligned over the full length of the sequence. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 60%, 65%, 70%, 75%, 80%, 85%, 90%, 91%, 92%, 93%, 94%, 95%, 96%, 97%, 98%, or 99% or more sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 65%, 70%, 75%, 80%, 85%, 90%, 91%, 92%, 93%, 94%, 95%, 96%, 97%, 98%, or 99% or more.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 60%, 65%, 70%, 75%, 80%, 85%, 90%, 91%, 92%, 93%, 94%, 95%, 96%, 97%, 98%, or 99% or more sequence identity to the reference sequence over a specified comparison window. Alignment can be conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Peptides that are "substantially similar" comprise a sequence with at least 60%, 65%, 70%, 75%, 80%, 85%, 90%, 91%, 92%, 93%, 94%, 95%, 96%, 97%, 98%, or 99% or more sequence identity or sequence similarity to the reference sequence over a specified comparison window. In this case residue positions that are not identical instead differ by conservative amino acid changes.

The 50 kD gamma-zein nucleotide sequence cloned from a maize endosperm cDNA library (Example 1) and disclosed in the present invention (SEQ ID NO:1) displays sequence similarity to the other two described corn gamma-zein genes, 27 kD gamma-zein (represented herein by GenBank Accession No. P04706) and 16 kD gamma-zein (represented herein by GenBank Accession No. AAA33523). The 50 kD gamma-zein was named due to its apparent molecular weight by migration in SDS-PAGE. This cDNA encodes a 295 amino acid protein and also shows sequence similarity to seed proteins of other plant species. For example, wheat alpha-gliadin (GenBank -ID:TAU51305, Accession No. U51305). The 50 kD gamma-zein DNA sequences isolated from different inbred lines showed an unusually low level of polymorphism. Only one single nucleotide polymorphism (SNP) (a 3 bp insertion) was detected along the entire cDNA sequence from DNA isolated from the inbred lines Mo17 and B73. The 50 kD gamma-zein gene has been located on chromosome 7, bin 7.03.

The 18 kD alpha-globulin nucleotide sequence was also cloned from a maize endosperm cDNA library (Example 5) and is disclosed in the present invention (SEQ ID NO:3). The 18 kD alpha-globulin was named due to its similarity to a rice seed globulin (rice alpha-globulin, GenBank Accession No. D50643). This cDNA encodes a 206 amino acid protein. Unlike the case of the 50 kD gamma-zein, there is no other maize gene known related to alpha-globulin in maize. The 18 kD alpha-globulin cDNA shows sequence similarity to seed proteins from other cereals including rice, wheat, and oats. Different maize inbred lines showed considerable allelism in the 18 kD alpha-globulin gene including SNP's. The 18 kD alpha-globulin gene has been located on chromosome 6, bin 6.05.

The 50 kD legumin 1 nucleotide sequence was also cloned from a maize endosperm cDNA library (Example 8) and is disclosed in the present invention (SEQ ID NO:5). The 50 kD legumin 1 was named due to its similarity to 11 S globulins found in other plant species: the so-called legumins. The 50 kD legumin 1 appears to be encoded by a single gene in the maize genome. It belongs to the 11S globulin superfamily and is closely related to legumins from other cereals (also called glutenins in rice and wheat or globulins in oat) and dicot plants. The 50 kD legumin polypeptide sequence is missing the evolutionary conserved 11S globulin pro-protein proteolytic site (Asn-Gly bond between the acidic chain and basic chain legumin regions) which makes it unique among the legumin protein superfamily. This cDNA encodes a 483 amino acid protein with a predicted N-terminal endoplasmic reticulum import signal peptide of 36 amino acids. The 50 kD legumin 1 DNA sequences isolated from different inbred lines showed a considerable level of polymorphism. The 50 kD legumin 1 gene has been mapped to chromosome 6, Bin 6.01.

The chromosomal location of the genes corresponding to the three cDNA's of the present invention have been determined as stated above. Knowing the map position of a gene is important and useful if it correlates with a trait, as is the case for the encoded polypeptides of the present invention. Certain alleles of these genes can, for instance, have an impact on seed hardness, starch extractability, energy availability, etc as is described in detail infra. Considerable knowledge has been accumulated regarding the so called Quantitative Trait Loci (QTL). Linkage of a gene to a QTL is of significance regarding the impact of this gene on the corresponding trait. Further, the map position can be used for marker assisted breeding, which is a very economical and time saving way to introduce alleles into elite germplasm. Alternatively, SNP's can also be used to screen a wide variety of germplasm for advantageous alleles.

The 50 kD gamma-zein protein of the present invention displays a high cysteine content and is therefore predicted to have a high number of disulfide bonds or high "disulfide status", as is observed for the other gamma-zein proteins. By "disulfide status" is intended the portion of cysteine residues within a protein that participate in disulfide bonds or disulfide bridges. Such disulfide bonds can be formed between the sulfur of a first cysteine residue and the sulfur of a second cysteine residue. It is recognized that such first and second cysteine residues can occur as part of a single polypeptide chain, or alternatively, can occur on separate polypeptide chains referred to herein as "inter-molecular disulfide bonds". When "disulfide status" is used in reference to a seed or part thereof, the "disulfide status" of such a seed or part thereof is the total disulfide status of the proteins therein.

The disulfide-rich, gamma-zein protein fraction in corn has been implicated as a major determinant of the poor amino acid content of this grain which contributes to its low nutrient content. In addition, as a result of the high-disulfide status of this gamma-zein fraction of corn endosperm it is also a significant contributor to the wet-milling properties of corn grain. For example, in the wet-milling process, the higher the number of disulfide bonds, the greater the requirement for chemical reductants to break these bonds and to maximize the release of starch granules. It is in this way that extensive disulfide bonding negatively impacts the process of wet-milling.

The intermolecular disulfide bridges of the gamma-zeins, along with the hydrophobic beta-zein, and alpha- and delta-zeins, are also important for the formation and maintenance of protein bodies. These protein bodies contribute to the physical properties of the grain that also affect the wet-milling process. In the wet-milling process, chemical reductants are required to break protein disulfide bonds to maximize starch yield and quality (Hoseney, 1994). The use in wet mills of odorous chemical such as sulfur dioxide and bisulfite requires extensive precautions and poses significant environmental problems (May, 1987).

Similar to that described for a decrease in the number of disulfide bonds, a decrease in the number of protein bodies can also be expected to improve the efficiency of the wet-milling process. Zein proteins interact during formation of protein bodies (through intermolecular disulfide bonds and hydropobic interactions), and these interactions are important for the formation of proteolytically stable complexes. A decrease in the expression of two or three gamma-zein genes can be expected to have an additive effect on the reduction of protein bodies resulting in a corresponding improvement in wet-milling properties.

The wet-milling properties of the corn grain of the present invention can be analyzed using a small-scale simulated wet-milling process incorporating or leaving out a reducing agent (bisulfite) in the steep water as used by Eckhoff et al., (1996, *Cereal Chem.* 73:54–57).

In addition to the positive impact that reducing agents have on the release of starch granules in the wet-milling process, it has also been shown that reducing agents can increase the dry matter digestibility of sorghum and corn and, thus, improve their feed properties. This result is supported by the results of data from in vitro digestibility assays described in the present invention (Examples 2–4) that demonstrate that reducing agents increase the dry matter digestibility or energy availability of corn. See also: Hamaker, B. R., et al 1987. Improving the in vitro protein digestibility of sorghum with reducing agents. *Proc. Natl. Acad. Sci. USA* 84: 626–628.

The "energy value", or "caloric value" of a feed or food, which is determined by energy density or gross energy (GE) content and by energy availability, is also termed "metabolizable energy (ME) content." (see Wiseman, J., and Cole, D. J. A. 1985.)

As used herein, "energy availability" means the degree to which energy-rendering nutrients are available to the animal, often referred to as energy conversion (ratio of metabolizable energy content to gross energy content). Energy availability can be determined with in vivo balance trials, in which excreta are collected by standard methodology (e.g., Sibbald, 1976; McNab and Blair, 1988; Morgan et al., 1975). Energy availability is largely determined by nutrient digestibility in the gastro-intestinal tract, although other factors such as absorption and metabolic utilization also influence energy availability.

"Digestibility" is defined herein as the fraction of the feed or food that is not excreted as feces. It can be further defined as digestibility of specific components (such as energy or protein) by determining the concentration of these components in the foodstuff and in the excreta. Digestibility can be estimated using in vitro assays, which is routinely done to screen large numbers of different food ingredients and plant varieties. In vitro techniques, including assays with rumen inocula and/or enzymes for ruminant livestock (e.g., Tilley and Terry, 1963; Pell and Schofield) and various combinations of enzymes for monogastric animals reviewed in Boisen and Eggum (1991) are also useful techniques for screening transgenic materials for which only limited sample is available.

The enzyme digestible dry matter (EDDM) assay used in these experiments as an indicator of in vivo digestibility is known in the art and can be performed according to the methods described in Boisen and Fernandez (1997) *Animal Feed Science and Technology* 68:83–92, and Boisen and Fernandez (1995) *Animal Feed Science and Technology* 51:29–43; which are herein incorporated in their entirety by reference. These data indicate that reducing the number of disulfide bonds in the seed of sorghum and corn can increase the dry matter digestibility of grain from these crops. It is also likely that a decrease in the disulfide-status of other grains would have a similar positive effect on their digestibility properties.

Although seed with extensive disulfide bonding exhibits poor wet-milling properties and decreased dry matter digestibility, a high disulfide-status has also been correlated with increased seed hardness and improved dry-milling properties. In fact, the transcript level of the 50 kD maize gamma-zein gene has been shown to be largely affected in several opacity mutants (o2, o5, and o9) and in opaque hordothionin-12 (U.S. Pat. No. 5,990,389) corn. These data indicate that this 50 kD maize gamma zein is a good gene candidate for altering other grain quality traits such as grain hardness. Assays for seed hardness are well known in the art and include such methods as those used in the present invention, described in Pomeranz et al. (1985) *Cereal Chemistry* 62:108–112; herein incorporated in its entirety by reference.

Based on its amino acid sequence, the 18 kD alpha-globulin can also be expected to have a high number of disulfide bonds and to participate in intermolecular protein cross-linking. For this reason, over-expression of the 18 kD alpha-globulin protein can be predicted to increase seed hardness. The ability to confer seed hardness is particularly useful in the case of soft kernel phenotypes that are induced by mutation or transgenic polypeptides. An increase in the levels of the 18 kD alpha-globulin can be used as a method for improving the dry-milling properties of soft kernel phenotypes.

In addition to its high cysteine content, the 18 kD alpha-globulin protein also possesses a relatively high percentage of the essential amino acids tryptophan (4.6% by weight, cysteine (5.1% by weight), and methionine (3.9% by weight). For this reason, transgenic over-expression of the 18 kD alpha-globulin protein can be expected to significantly increase the percentage of tryptophan and sulfur-containing amino acids in corn grain and, thus, increase the nutritional value of the grain.

The "nutritional value" of a feed or food is defined as the ability of that feed or food to provide nutrients to animals or humans. The nutritional value is determined by 3 factors: concentration of nutrients (protein & amino acids, energy, minerals, vitamins, etc.), their physiological availability during the processes of digestion, absorption and metabolism, and the absence (or presence) of anti-nutritional (e.g., toxic) compounds.

Similar to the 18 kD alpha-globulin, the 50 kD legumin 1 protein also possesses a relatively high percentage of essential amino acids. This protein contains 6.7%, 0.7%, 2.2%, 1.1%, 3.6%, and 2.7% by weight of lysine, tryptophan, methionine, cysteine, isoleucine, and threonine, respectively. For this reason, transgenic over-expression of the 50 kD legumin 1 protein can also be expected to increase the nutritional value of the grain.

In addition to its desirable amino acid content, the 50 kD legumin 1 protein is assembled differently than other legumin polypeptides. As a result of the missing proteolytic cleavage site, the 50 kD legumin 1 protein is not cleaved into acidic and basic chains. Instead this legumin assembles into 9S polypeptide primers (presumably in the endoplasmic reticulum) and does not undergo assembly into 11S globulin hexamers. The assembly properties of this 50 kD legumin 1 polypeptide could contribute to unique food processing properties of protein extracts from seed expressing this protein. For example, the 50 kD legumin 1 polypeptide could be ectopically expressed in soybean seed and protein isolates from corresponding soybean seed display altered functionalities such as solubility under acidic conditions, improved water-holding capacity and the like.

Another feature of the 50 kD legumin 1 polypeptide is a string of histidine residues that can function as a metal binding site. Native 50 kD legumin 1 polypeptide binds with high affinity to nickel chelation columns. This property can be used to purify corn legumin 1 in bulk from complex protein mixtures and to purify other polypeptides of interest through the production of fusion proteins. The metal chelation properties of the 50 kD legumin 1 polypeptide could also be of importance for bio-remediation or food health (antioxidant) applications.

It has also been demonstrated that proteolytic digestion of the alcohol-soluble seed protein fraction (prolamins) from wheat, barley, oats, and rye is known to give rise to biologically active, anti-nutritional peptides able to adversely affect the intestinal mucosa of coeliac patients (Silano and Vincenzi (1999) *Nahrung* 43:175–184). Furthermore, the alpha-, beta-, and gamma-gliadins present in the prolamin-like protein fraction of wheat are capable of inducing coeliac disease (Friis et al. (1994) *Clin. Chim. Acta.* 231:173–183). The alpha-gliadin and gamma-gliadin from wheat have also been identified as major allergens (Maruyama et al. (1998) *Eur. J. Biochem.* 256:604. For these reasons the methods of the present invention are also directed to the elimination or the reduction of the levels of at least one seed protein in wheat, barley, oats, or rye to produce a grain with eliminated or reduced anti-nutritional or allergenic properties.

The compositions of the invention are useful for modulating the levels of at least one seed protein in seeds. By "modulate" is defined herein as an increase or decrease in the level of a seed protein within seed of a genetically manipulated plant relative to the level of that protein in seed from the corresponding wild-type plant (i.e., a plant not genetically manipulated in accordance with the methods of the present invention). In a first embodiment, methods are particularly directed to reducing the level the 16 kD, the 27 kD protein and the 50 kD gamma-zein proteins to improve the nutritional value and industrial use of grain. A second embodiment is directed to the reduction or elimination of the alpha-, beta-, and gamma-gliadins of wheat, barley, rye, and oats to eliminate or ameliorate the anti-nutritional or allergenic effects of these proteins. In another embodiment, the levels of the alpha-globulin protein or the legumin 1 protein in plant seed are either increased or decreased to affect the nutritional value, or the hardness of the seed. Other embodiments of the invention include methods directed to screening for particular plant phenotypes based on antibodies specific for the polypeptides of the invention, or using SNP's of the nucleotide sequences of the invention.

Reduction of the level of the 16 kD, the 27 kD protein or the 50 kD gamma-zein proteins in plant seed can be used to improve the nutritional value and industrial use of such grain. By reducing the level of the 27 kD gamma-zein gene (Accession No. P04706) in maize seed, seed plants having improved amino acid composition can be obtained. Lysine content can be increased at least 10%, 15%, 20%, 30%, 40% or greater. The methods of the invention are also useful for producing grain that is more rapidly and extensively digested than grain with normal gamma-zein protein levels.

Because the 27 kD gamma-zein suppression trait is dominant or semi-dominant, improvements in grain digestibility can be obtained by introducing it into specific pollinators (i.e., high oil corn) using conventional methods and/or the top-cross technology found in U.S. Pat. No. 5,704,160. In addition, reducing the levels of other seed proteins, such as beta-zein, in conjunction with suppression of one or more gamma-zein genes can result in further grain improvement including lysine content and digestibility.

Thus, suppression of gamma-zein genes can be used to increase the nutritional value of seed, particularly by increasing the lysine content of the seed, and the digestibility of seed. Reduction in the gamma-zein levels in such seed can be at least about 20%, 30%, 40%, 50%, 60%, 70%, 80%, 90% and up to 100%. Increases in the lysine content of such seed can be at least about 10%, 15%, 20%, 25%, 30%, 35%, 40%, 45%, and 50% or higher. Digestibility can be improved by at least 3%, 6%, 9%, 12%, 15%, 20% and greater.

Methods of the invention are also directed to the reduction or elimination of the expression of one or more specific prolamin-like proteins in the seed from wheat, barley, oats, and rye that are known to give rise to biologically active, anti-nutritional peptides. These proteins include, but are not limited to, the alpha-, beta-, and gamma-gliadins of wheat. Grain and grain products possessing reduced levels of these proteins would not possess such negative characteristics as the ability to induce coeliac disease and an allergic response.

It is noted that modifications made to the grain by the present invention do not compromise grain handling properties with respect to mechanical damage. Mechanical damage to grain is a well-described phenomenon (e.g., McKenzie, 1985) that contributes to dust in elevators and livestock facilities, and which may increase susceptibility to pests; Grain damage can be quantified and assessed by objective measures (e.g., Gregory et al., 1991) such as kernel density and test weight. See also: McKenzie, B. A. 1985.

The invention also encompasses modulation of an 18 kD alpha-globulin protein or a legumin 1 protein to affect the nutritional value and/or the hardness of plant seed. A decrease in or an elimination of the expression of at least one of these proteins results in seed with decreased nutritional value. Such grain has applications for use in diet food products. Alternatively, an increase in the levels of these proteins in plant seed would result in an increase in the nutritional value of the seed. The levels of the maize 18 kD alpha-globulin protein (SEQ ID NO:4) can be increased in maize seed, resulting in seed that can be predicted to possess at least about 20%, 30%, 40%, 50%, 60%, 70%, 80%, 90%, 100%, 110%, 120%, 130%, 140%, 150%, and up to a 300% increase in tryptophan and sulfur-containing amino acids relative to grain of wild-type plants. The level of the 50 kD legumin 1 protein can be similarly increased in maize seed to increase the level of essential amino acids in the grain. Food products and feed based on such seed will have a higher nutritional value based on the increased levels of essential amino acids.

In addition to the increase in nutritional value, an increase in the level of the 18 kD alpha-globulin protein in plant seed can be predicted to result in grain possessing increased hardness. This is due to an increase in disulfide bond status relative to grain from wild-type plants, and has applications for improving the dry-milling properties of such modified grain. Introduction of this trait into corn plants with soft kernel phenotypes, particularly soft kernel phenotypes induced by the introduction of other transgenic polypeptides including, but not limited to, hordothionin 12 (U.S. Pat. No. 5,990,389), can ameliorate or eliminate the undesirable dry-milling properties of such soft kernel grain by increasing seed hardness.

In another embodiment, the levels of the 50 kD legumin 1 polypeptide are increased in plant seed for the purpose of increasing the metal chelating properties of the seed. The unique string of histidine residues present in the 50 kD legumin 1 polypeptide function as a metal chelating site. Products produced from such seed could be used for bioremediation or in food health (antioxidant) applications.

Methods are provided for modulating the level of at least one seed protein in plant seed including, but not limited to, the 50 kD gamma-zein (SEQ ID NO:2), the 18 kD alpha-globulin (SEQ ID NO:4), the legumin 1 (SEQ ID NO:6), the 27 kD gamma-zein (Accession No. P04706), the 16 kD gamma-zein (Accession No. AAA33523), the 15 kD beta-zein (Accession No. P06673), the gamma-kafarins, and the alpha-, beta-, and gamma-gliadins. The methods of the invention comprise the use of transgenic expression, antisense suppression, co-suppression, mutagenesis including transposon tagging, and biosynthetic competition, alone or in combination. Depending upon the intended goal, the level of at least one seed protein may be increased, decreased, or eliminated entirely as described below. Methods of the invention can be utilized to alter the level of any seed protein found within a particular plant species, including the alpha-, beta-, delta-, gamma-zeins of maize, and alpha-globulins of maize, the legumin 1 and other seed proteins of maize, rice and sorghum, and the alpha-, beta-, and gamma-gliadins of wheat, barley, rye, and oats. "Alter" and "modulate" are herein used interchangeably.

In many instances the seed coding sequences for use in the methods of the present invention, are provided in "expression cassettes" for expression in the plant of interest. The expression cassette will include 5' and 3' regulatory sequences operably linked to at least one of the sequences of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case where an expression cassette contains two protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The methods of transgenic expression can be used to increase the level of at least one seed protein in grain. The methods of transgenic expression comprise transforming a plant cell with at least one expression cassette comprising a promoter that drives expression in the plant operably linked to at least one nucleotide sequence encoding a seed protein. Methods for expressing transgenic genes in plants are well known in the art.

The methods of transgenic co-suppression can be used to reduce or eliminate the level of at least one seed protein in grain. The methods of transgenic co-suppression comprise transforming a plant cell with at least one expression cassette comprising a promoter that drives expression in the plant operably linked to at least one nucleotide sequence transcript in the sense orientation encoding at least a portion of the seed protein of interest. By "co-suppression" is intended the use of nucleotide sequences in the sense orientation to suppress the expression of the corresponding endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, at least about 65%, 70%, 75%, 80%, 85%, 90%, 91%, 92%, 93%, 94%, 95%, 96%, 97%, 98%, or 99% or more sequence identity. See U.S. Pat. Nos. 5,283,184 and 5,034,323; herein incorporated by reference.

The endogenous gene targeted for co-suppression may be a gene encoding any seed protein that accumulates as a seed protein in the plant species of interest, including, but not limited to, the seed genes noted above. For example, where the endogenous gene targeted for co-suppression is the 50 kD gamma-zein gene disclosed herein, co-suppression is achieved using an expression cassette comprising the 50 kD gamma-zein gene sequence, or variant or fragment thereof.

Additional methods of co-suppression are known in the art and can be similarly applied to the instant invention. These methods involve the silencing of a targeted gene by intron-spliced hairpin RNA's (see Smith et al.(2000) *Nature* 407:319–320, and Patent Applications WO 98153083 and WO 99/53050).

The methods of antisense suppression can be used to reduce or eliminate the level of at least one seed protein in grain. The methods of antisense suppression comprise transforming a plant cell with at least one expression cassette comprising a promoter that drives expression in the plant cell operably linked to at least one nucleotide sequence that is antisense to a nucleotide sequence transcript of such a gamma-zein gene. By "antisense suppression" is intended as the use of nucleotide sequences that are antisense to nucleotide sequence transcripts of endogenous plant genes to suppress the expression of those genes in the plant.

Methods for suppressing gene expression in plants using nucleotide sequences in the antisense orientation are known in the art. The methods generally involve transforming plants with a DNA construct comprising a promoter that drives expression in a plant operably linked to at least a portion of a nucleotide sequence that is antisense to the transcript of the endogenous gene. Antisense nucleotides are constructed to hybridize with the corresponding mRNA. Modifications of the antisense sequences may be made as long as the sequences hybridize to and interfere with expression of the corresponding mRNA. In this manner, antisense constructions having at least about 70%, 75%, 80%, 85%, 90%, 91%, 92%, 93%, 94%, 95%, 96%, 97%, 98%, or 99% or more sequence identity to the corresponding antisense sequences may be used. Furthermore, portions, rather than the entire nucleotide sequence, of the antisense nucleotides may be used to disrupt the expression of the target gene. Generally, sequences of at least 50 nucleotides, 100 nucleotides, 200 nucleotides, or greater may be used.

The methods of transposon tagging can be used to reduce or eliminate the level of at least one seed protein in grain.

The methods of transposon tagging comprise insertion of a transposon within an endogenous plant seed gene to reduce or eliminate expression of the seed protein. By "seed gene" is meant the gene that corresponds to the particular seed cDNA of interest. For example, by "50 kD gamma-zein gene" is meant the gene that corresponds to the cDNA set forth in SEQ ID NO:1.

In this method, a decrease or elimination of the expression of the seed protein of the invention is the goal, and insertion of a transposon within a regulatory region of this gene, in addition to, or rather than, an insertion within the seed-protein coding sequence, may result in decreased expression of the seed protein. For this reason, a transposon that is within an exon, intron, 5' or 3' untranslated sequence, a promoter, or any other regulatory sequence of, for example, the gamma-zein gene corresponding to the 50 kD gamma-zein cDNA of the invention, that results in decreased expression of the gamma-zein protein, is also an object of this embodiment.

Methods for the transposon tagging of specific genes in plants are well known in the art (see for example, Maes et al. (1999) Trends Plant Sci. 4:90–96; Dharmapuri and Sonti (1999) FEMS Microbiol. Lett. 179:53–59; Meissner et al. (2000) Plant J. 22:265–274; Phogat et al. (2000) J. Biosci. 25:57–63; Walbot (2000) Curr. Opin. Plant Biol. 2:103–107; Gai et al. (2000) Nuc. Acids Res. 28:94–96; Fitzmaurice et al. (1999) Genetics 153:1919–1928). In addition, the TUSC process for selecting Mu-insertions in selected genes has been described (Bensen et al. (1995) Plant Cell 7:7584; Mena et al. (1996) Science 274:1537–1540; U.S. Pat. No. 5,962,764, which is herein incorporated by reference).

Other methods for decreasing or eliminating the expression of endogenous genes are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted (for examples of these methods see Ohshima, et al. (1998) Virology 243:472–481; Okubara et al. (1994) Genetics 137:867–874; Quesada et al. (2000) Genetics 154:421–436. In addition, a fast and automatable method for screening for chemically induced mutations, TILLING, (Targeting Induced Local Lesions in Genomes), using a denaturing HPLC or selective endonuclease digestion of selected PCR products is also applicable to the instant invention (see McCallum et a. (2000) Nat. Biotechnol. 18:455–457).

Methods of biosynthetic competition with other high-sulfur-containing proteins are used to reduce the levels of at least one seed protein in plant seed. The methods of biosynthetic competition comprise transforming plant cells with at least one expression cassette comprising a promoter that drives expression in the plant cell operably linked to at least one nucleotide sequence encoding a protein selected from the group consisting of delta-zeins, hordothionin 12, and other naturally occurring or engineered high-sulfur-containing proteins. In some cases the competing protein may possess a high lysine content in addition to a high sulfur content to further increase the nutritional value of the grain.

Biosynthetic competition of seed proteins with other sulfur-rich proteins occurs naturally. This natural process can be manipulated to reduce the levels of certain seed proteins, because the synthesis of some seed proteins is transcriptionally and/or translationally controlled by the nitrogen and/or sulfur supply in the developing seed. The expression of recombinant polypeptides, including the ectopic (transgenic) expression of seed proteins or other high-sulfur-, high-nitrogen-containing proteins, can have a substantial impact on intracellular nitrogen and sulfur pools. Thus, the expression of these proteins can result in suppression of the expression of other seed proteins such as, for example, the high-sulfur containing gamma-zein proteins.

Plant transformants containing a desired genetic modification as a result of any of the above described methods resulting in increased, decreased or eliminated expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

Another embodiment is directed to the screening of transgenic maize plants for specific phenotypic traits conferred by the expression, or lack thereof, of the 50 kD gamma-zein, the 18 kD alpha-globulin, or the 50 kD legumin 1 polypeptides of the invention. The specific phenotypic traits for which this method finds use include, but are not limited to, all of those traits listed herein, supra. Maize lines can be screened for a particular phenotypic trait conferred by the presence or absence of the 60 kD gamma-zein, the 18 kD alpha-globulin, or the 50 kD legumin 1 protein using an antibody that binds selectively to one of these polypeptides. In this method, tissue from the maize line of interest is contacted with an antibody that selectively binds the seed-protein polypeptide for which the screen is designed The amount of antibody binding is then quantified and is a measure of the amount of the seed-protein polypeptide present in the maize line. Methods of quantifying polypeptides by immunodetection in this manner are well known in the art.

An additional embodiment is directed to the use of the 50 kD legumin 1 protein to purify a polypeptide of interest based on the metal chelating properties of the 50 kD legumin 1 polypeptide. In this case recombinant DNA techniques known in the can be used to produce an expression cassette encoding a heterologous polypeptide consisting of the 50 kD legumin 1 polypeptide or a fragment thereof fused to a polypeptide of interest. The expression cassette can be introduced into either a eucaryotic or a bacterial host cell and the protein expressed in the host cell. The protein can then be isolated from the cells by an appropriate purification scheme using standard metal chelating column techniques such as high affinity nickel chelating columns that are commercially available. The legumin 1 nucleotide sequence can be fused to either the N-terminus or C-terminus of the nucleotide sequence encoding the polypeptide of interest.

In the practice of certain specific embodiments of the present invention, a plant is genetically manipulated to have a suppressed or increased level of one or more seed proteins in seed and/or to ectopically express one or more seed or other high-sulfur, high-lysine-containing protein. Those of ordinary skill in the art realize that this can be accomplished in any one of a number of ways. For example, each of the respective coding sequences for such proteins can be operably linked to a promoter and then joined together in a single continuous fragment of DNA comprising a multigenic expression cassette. Such a multigenic expression cassette can be used to transform a plant to produce the desired outcome utilizing any of the methods of the invention including sense and antisense suppression and biosynthetic competition. Alternatively, separate plants can be transformed with expression cassettes containing one of the desired set of coding sequences. Transgenic plants resulting from any or a combination of the methods of the invention including transgenic expression, co-suppression, antisense suppression, mutagenesis including transposon tagging, and biosynthetic competition that express the desired activity can be selected by standard methods available in the art. These methods include, but are not limited to, methods such as immunoblotting using antibodies which bind to the proteins of interest, SNP analysis, or assaying for the products of a reporter or marker gene, and the like. Then, all of the desired coding sequences and/or transposon tagged sequences can be brought together into a single plant through one or more rounds of cross pollination utilizing the previously selected transformed plants as parents.

The seed coding sequences for use in the methods of the present invention are provided in expression cassettes for expression in the plant of interest. Such expression cassettes are provided with a plurality of restriction sites for insertion of the 50 kD gamma-zein, the 18 kD alpha-globulin, the 50 kD legumin 1 sequence or any other sequence of the present invention to be placed under the transcriptional regulation of the regulatory regions. The expression cassettes may additionally contain selectable marker genes.

The expression cassette will include in the 5'-3' direction of transcription, a transcriptional and translational initiation region, the 50 kD gamma-zein, the 18 kD alpha-globulin, or the 50 kD legumin 1 DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the 50 kD gamma-zein, the 18 kD alpha-globulin, or the 50 kD legumin 1 gene in the plant or plant cell. Thus, the phenotype of the plant or plant cell is altered.

The termination region may be native with the transcriptional initiation region, may be native with the operably linked DNA sequence of interest, or may be derived go from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, for example, as in the case of engineered high-sulfur-containing proteins for the method of biosynthetic competition, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al.(1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480483; Gossen (1993) Ph.D Thesis, University of Heidelberg; Reines et al. (1993) *Proc. Natl. Acad. Sci. USA*

90:1917–1921;: Labow et al. (1990) *Mol. Cell. Biol.* 10:3343–3356; Zambretti et al. (1992) *Proc. Natl. Acad. Sci. USA* 89:3952–3956; Baim et al.(1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Veriag, Berlin); Gill et al. (1988) *Nature* 334:721–724. Such disclosures are herein incorporated by reference.

The above list of selectable marker genes is not meant to be limiting. Any selectable marker gene can be used in the present invention.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al.(1999) *Proc. Natl. Acad. Sci. USA* 96:8774–8778; herein incorporated by reference.

A number of promoters can be used in the practice of the invention. The promoters can be selected based on the desired outcome. The nucleic acids can be combined with constitutive, tissue-preferred, or other promoters for expression in plants, more preferably a promoter functional during seed development.

Such constitutive promoters include, for example, the core promoter of the Rsyn7 promoter and other constitutive promoters disclosed in WO 99/43838; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675489); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize ln2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced protein expression within a particular plant tissue. Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):1 57–168; Rinehart et al. (1996) *Plant Physiol.* 112(3):1 331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.*

20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kD zein); milps (myo-inositol-1-phosphate synthase); and celA (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glb-1 is a preferred embryo-specific promoter. For dicots, seed-specific promoters include, but are not limited to, bean phaseolin, napin, β-conglycinin, soybean lectin, cruciferin, and the like. For monocots, seed-specific promoters include, but are not limited to, maize 15 kD zein, 22 kD zein, 27 kD zein, 10 kD delta-zein, waxy, shrunken 1, shrunken 2, globulin 1, etc.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, the copending application entitled "Constitutive Maize Promoters," U.S. application Ser. No. 09/257,584, filed Feb. 25, 1999, and herein incorporated by reference.

Methods of the invention can be utilized to alter the level of at lease one seed in seed from any plant species of interest. Plants of particular interest include grain plants that provide seeds of interest including grain seeds such as corn, wheat, barley, rice, sorghum, rye, oats, etc. The present invention may be used for many plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), oats, and barley.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840; Cai et al., U.S. patent application Ser. No. 09/056,418), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, New York), pp. 197–209 (pollen); Kaeppler et al. (1990) *Plant Cell Reports* 9:415–418 and Kaeppler et al. (1992) *Theor. Appl. Genet* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via Agrobacterium tumefaciens); all of which are herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant The nucleotide constructs of the invention may be introduced into plants by contacting plants with a virus or viral nucleic acids. Generally, such methods involve incorporating a nucleotide construct of the invention within a viral DNA or RNA molecule. It is recognized that the protein of interest of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways, under plant forming conditions. See, for example, McCormick et al. (1986) *Plant Cell Reports* 5:81–84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In addition, the desired genetically altered trait can be bred into other plant lines possessing other desirable characteristics using conventional breeding methods and/or top-cross technology. The top-cross method is taught in U.S. Pat. No. 5,704,160 herein incorporated in its entirety by reference.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described infra for selecting transformed plants. If necessary, the selected progeny can be used as either the pollen donor or pollen recipient in a subsequent cross pollination.

Existing maize strains possessing desirable traits can be engineered to provide increased energy availability with the methods of this invention. While the methods of the invention do not depend on any particular biological mechanism experimental results indicate that the increased energy availability of the corn kernel genetically modified to contain reduced levels of gamma-zein proteins is likely a result of reduced grain disulfide content. It has been shown that the response in digestibility to the treatment of grain with DTT is inversely related to the digestibility of untreated grain (Boisen and Eggum, 1991).

Digestibility of immature grain (grain at late dough or silage maturity stage) is equally improved by pretreatment with reducing agents (DTT) as mature grain. The same can be expected for low gamma zein corn as the effects of DTT pretreatment, and low gamma zein corn, on digestibility are virtually the same. Improvements in digestibility of immature grain through the methods of the present invention can be extrapolated to improvements in digestibility of silage— about half of which consists of immature grain. The improvements in digestibility with DTT pretreatment is inversely related to the intrinsic digestibility of untreated grain. For this reason, corn lines of low intrinsic digestibility (i.e. high gamma zein levels) can be expected to be more amenable to genetic modification through the method of the invention than those of higher digestibility (i.e. low gamma zein levels). This aspect of the invention enables those of skill in the art of breeding to make rapid advances in introgressing a low gamma zein trait into the appropriate elite germplasm.

This invention allows for the improvement of grain properties such as increased digestibility/nutrient availability, nutritional value, silage quality, and efficiency of wet or dry milling in maize strains already possessing other desirable characteristics.

Corn grain with reduced gamma-zein protein content offers the following advantages:

First, ground corn grain with a reduced gamma-zein protein content offer increased energy availability and protein digestibility to monogastric livestock (see Example 2). "Monogastric animals" include but are not limited to: pigs, poultry, horses, dogs, cats, rabbits and rodents.

It can be deduced from analysis of the in vitro experimental data provided herein that the corn grain from maize genetically altered to contain reduced gamma-zein protein levels will have a 5% increase in metabolizable energy for poultry and pigs. Using this assumption the following replacement value can be assigned to the high energy availability trait in grain resulting from the gamma-zein gene knock-out. Five percent of 1665 kcal/lb equals about 83 kcal/lb. Taking into account that a bushel of corn contains 5660 lbs, the 83 kcal/lb difference amounts to a gain of 4650–5000 kcal/bu. This difference in available energy is equivalent to 1.3–1.4 lb fat, which, at 12 cts/lb, is worth 15–17 cents per bushel.

Second, corn grain with a reduced gamma-zein protein content possess improved ruminant (e.g.: cattle sheep, and goats) feed quality through increased digestibility (see Example 2). Grain is fed to ruminants in minimally processed form, and the rigid protein structure of corn endosperm has been shown to constitute a large impediment to microbial digestion in the rumen, which can be partly overcome by predigestion with protease (McAllister et al. (1993) *J. Anim. Sci.* 71:205–212). A reduced gamma-zein protein content imparts a similar or even larger improvement to ruminal digestion of whole corn.

Third, corn grain with reduced levels of gamma-zein proteins has an increased response to feed processing. The nutrient availability from whole corn grain can be increased by extensive processing (steam-flaking or extrusion) resulting in starch gelatinization and protein disulfide bond reduction (Blackwood and Richardson, 1994). The response to processing is sometimes lower than expected. The heat and/or shearing force applied during processing causes rearrangements of protein disulfide bonds, which may partly counteract the improvement in digestibility resulting from starch gelatinization. The response to steam-flaking of corn and sorghum grain is negatively correlated with protein disulfide content (Blackwood and Richardson, 1994). For low gamma zein corn or low gamma kafarin sorghum the extent of disulfide rearrangements during processing is reduced, which allows for a more uniform response to steam-flaking, and which can be expected to reduce the energy required in steam-flaking or grinding processes.

Fourth, corn grain with a lower gamma-zein protein content has improved silage quality for dairy cattle, especially for silage harvested at late maturity. Although silage is harvested at earlier maturity than grain, a certain degree of dry-down (and protein disulfide formation) has already occurred by the time the crop is ensiled, especially under dry and hot conditions. Our work has shown that pretreatment with a reducing agent of immature, dough-stage corn kernels, sampled at silage maturity, resulted in drastically improved in vitro digestibility, a strong indication that the protein disulfide imposed barriers to digestion had already been established. (data in Example 2) Hence, the digestibility of the "yellow portion" of corn silage can be expected to be higher for grain with a reduced gamma-zein protein content. Increased digestibility will be especially notable in the case of silage made from mature corn and for high-yielding dairy cows in which high passage rates do not allow for extensive ruminal digestion.

Fifth, corn grain with a reduced gamma-zein protein content will have an increased efficiency of wet milling. An increase in wet-milling efficiency and starch recovery can be expected due to the lower disulfide content of grain with reduced gamma-zein protein content. Efficiencies in the processes of wet milling also include reduced steeping time and/or reduced need for chemical reductants such as sulfur dioxide and sodium bisulfite. The use of fewer chemicals will improve wet-milling economics and reduce environmental pollution.

EXAMPLES

Maize lines (transgenic and transposon-mutagenized) have been developed with increased or decreased levels of specific endosperm proteins. For several of the obtained lines, experimental evidence indicates that the introduced changes result in improved grain properties.

Example 1

Cloning and Transgenic Co-suppression of a Novel Maize 50 kD Gamma-Zein

A 50 kD gamma-zein nucleotide sequence was cloned from a maize endosperm cDNA library (mid and late development). Based on EST numbers 50 kD gamma-zein transcripts are relatively abundant (compared to other seed protein transcripts) and represent approximately 0.5% of the endosperm mRNA during mid development. A large variation in the abundance of 50 kD gamma-zein transcripts has been observed between different inbred lines (transcript profiling results). The 50 kD gamma-zein gene has been located on chromosome 7, bin 7.03

The 50 kD gamma-zein cDNA sequences isolated from different inbred lines show an unusually low level of polymorphism. Only one SNP (a 3 bp insertion) was detected along the entire cDNA sequence from DNA isolated from the inbred lines Mo17 and B73 (the SNP is bold and in lower case). See also SEQ ID NOS: 7 and 8.
50 kD gamma-zein, B73 partialCCAGCAGCAGCAACACCAA-
CAACAACAAGTTCACATGCAACCA-
CAAAAACATCAGCAACAACAAGAAGT-
TCATGTTCAACAACAACAACAACAACCGCAGCACCA
ACAACAACAACAACAACAacaGCACCAA-
CAACAACATCAATGTGAAGGCCAACAA-
CAACATCACCAACAATCACAAGGCCAT-
GTGCAACAACACGAACAGAGCCATGAGCAACACCAA
GGACAGAGCCATGAGCAACAACATCAA-
CAACAATTCCAGGGTCATGACAAGCAG-
CAACAACCACAACAGCCTCAGCAATAT-
CAGCAGGGCCAGGAAAAATC 50 kD gamma-zein, Mo17 partial CCAGCAGCAGCAACACCAACAACAA-
CAAGTTCACATGCAACCACAAAAACAT-
CAGCAACAACAAGAAGTTCATGTTCAACAACAACAA
CAACAACCGCAGCACCAACAACAACAACAACAAC
A\*\*\*GCACCAACAACAACATCAATGTGAAGGCCAACA
ACAACATCACCAACAATCACAAGGCCAT-
GTGCACAACACGAACAGAGCCATGAG-
CAACACCAAGGACAGAGCCATGAGCAA-
CAACATCAACAACAATTCCAGGGTCATGACAAGCAGC
AACAACCACAACAGCCTCAGCAATAT-
CAGCAGGGCCAGGAAAAATC The 50-kD gamma zein transformation event described herein was one of various high-digestibility events produced. The event was generated with a construct containing the 27 kD gamma zein promoter, 50 kD gamma zein ORF in sense orientation, and 27-kD gamma zein terminator using particle bombardment. It was found to be reduced in all known gamma zein proteins, i.e., 50 kD-, 27 kD-, and 16 kD-gamma zein. Protein gel & 50 kD gamma zein Western blots of segregating CS50 events were performed to confirm co-suppression. The kernel phenotype of the transgenic seed was normal (i.e., vitreous).

Segregating kernels from transgenic corn co-suppressed in 50 kD gamma zein were ground to a fine meal and subjected to the monogastric in vitro digestibility assay to determine Enzyme Digestible Dry Matter (EDDM). EDDM of 50 kD gamma zein co-suppressed grain was improved by 3.0 percentage units. An overnight soak in 10 mM of the strong reducing agent dithiothreietol (DTT), known to maximize in vitro digestibility, improved digestibility slightly beyond that reached with 50 kD gamma zein co-suppression (by 1.4 percentage units.

Example 2

Transgenic Co-suppression of 27 kD Gamma-Zein

Events in which the expression level of 27 kD gamma-zein protein was reduced to less than 5% of wild-type as determined by SDS-PAGE and immunoblotting were obtained with two transgenes. The endosperm protein profiles of grain in which the 27 kD gamma-zein gene was co-suppressed showed an additional reduction of approximately 60% in the level of the 16 kD gamma-zein protein and an approximate five-fold increase in the level of the hydrophobic 15 kD beta-zein protein. The overall lysine content in this grain increased by 15–30. Even with the significant decrease in high disulfide containing gamma-zein proteins, grain from these events showed a normal (vitreous) phenotype and were of unaltered test weight and hardness. This result was unexpected as the decrease in the disulfide content, and specifically the decrease in gamma zein, might have been expected to A result in grain with a soft phenotype (see Lopez and Larkins, 1991). Assays for seed hardness are well known in the art and include such methods as those used in the present invention, described in Pomeranz et al. (1985) *Cereal Chemistry* 62:108–112, herein incorporated in its entirety by reference.

The co-suppression trait is shown to be dominant. Various normal and transgenic maize lines, as well as commercial hybrids, have been pollinated with pollen from the gamma-zein co-suppressing events with the result of total suppression of gamma-zein protein in the hemizygous endosperm as determined by SDS-PAGE and immunoblotting. Therefore, the gamma-zein gene co-suppression trait can be introduced into specific pollinators (i.e., high oil corn) using conventional methods and/or the topcross technology found in U.S. Pat. No. 5,704,160.

$T_3$-segregating grain was phenotyped for gamma-zein protein levels and were divided into two samples, one with wild-type gamma-zein protein levels and a second with reduced gamma-zein protein levels (less than 10% of wild-type). Ground corn from both samples was subjected to an in vitro energy availability assay. The enzyme digestible dry matter (EDDM) assay used in these experiments as an indicator of in vivo digestibility, is known in the art and was performed using enzymes, buffers, and digestion conditions described in Boisen and Fernandez (1997) *Animal Feed Science and Technology* 68:83–92; and Boisen and Fernandez (1995) *Animal Feed Science and Technology* 51:29–43, which are herein incorporated in their entirety by reference. The results clearly indicated that ground corn from gamma-zein co-suppressed grain were more rapidly and extensively digested than corn with normal gamma-zein protein levels, by as much as 20% at the 4 hour time point.

The role of disulfide bridges in the digestion of corn was investigated in gamma-zein gene co-suppressed versus control grain. As expected, pretreatment with a strong reducing agent (10 mM DTT) increased the enzyme digestible dry matter (EDDM) level (4 hour digestion) of control grain by 16% but not that of the gamma-zein gene co-suppressed grain. A similar result was observed for various low gamma-zein TopCross hybrids (e.g.: with grain hybrids 3394 and 32J55). Hence, the impact of DTT on digestibility apparently involves the reduction of disulfides of cysteine residues in gamma-zein proteins. Phenotyped kernel samples (those with normal levels of 27 kD gamma-zein protein and those with low levels of 27 kD gamma-zein protein) from segregating ears from the same events were analyzed using a small-scale simulated wet-milling process incorporating or leaving out a reducing agent (bisulfite) in the steep water (Eckhoff et al., (1996) *Cereal Chem.* 73:54–57). Similar to the digestibility assay, the reductant had a lesser impact on starch extractability in grain containing low levels of 27 kD gamma-zein protein compared to wild-type grain.

Rumen in situ dry matter digestibility of co-suppressed (i.e. low) 27 kD gamma zein corn in a top-cross onto Pioneer grain hybrid 3394 was compared with a control top-cross and with the grain parent. Coarsely ground mature grain samples were weighed into pre-tared nylon bags (4 replicates each). The bags were sealed and placed in the rumen of a fistulated steer for 18 hrs, then washed to remove microbial mass, ovendried, and weighed. Ruminal digestibility of the low gamma zein grain was 18% higher than the control topcross and 10% higher than that of the grain parent. See also: Nocek, J. E. 1988. In situ and other methods to estimate ruminal protein and energy digestibility. *J. Dairy Sci.* 71 :2051–2069.

The same samples subjected to the in situ digestion procedure were also evaluated by an automated in vitro gas production method as described by Pell and Schofield (1993).

The in vitro gas production curve comparing low gamma zein topcross to the grain parent and a control cross showed a higher gas production volume for the low gamma zein topcross, corresponding to a more rapid and extensive digestion of the low gamma-zein grain in rumen fluid. Coarsely ground mature grain samples were weighed into fermentation flasks (9 replicates each). The flasks were inoculated with buffered rumen fluid and incubated at 38° C. for 24 hrs, during which the volume of the fermentation gas was automatically recorded. Average gas production was clearly higher for low gamma zein topcross than for each of the two controls.

Immature kernels of various wild-type inbreds & hybrids, sampled at various stages of seed development and maturation, consistently respond to DTT pretreatment in the monogastric in vitro assay when sampled 1 month after pollination or later The improvement in digestibility with DTT points at a consistent inhibitory role of protein disulfide bonds on digestibility of wild-type kernels from about 28 DAP onwards. From these results one can conclude that kernels harvested at dough stage or silage maturity (approximately 40–45 DAP) would benefit from reduced gamma zein levels. We also applied DTT pretreatment prior to monogastric in vitro digestion of 27 kD gamma zein co-suppressed immature kernels (33 DAP), with no apparent effect, similar to our observations for low gamma zein mature grain. Given the response to DTT for wild-type immature kernels from 28 DAP through maturity, the lack of DTT response for low gamma zein kernels of any maturity, and the observed improvements in ruminal digestibility of mature low gamma zein grain, one can deduce, with very high likelihood, that ruminal digestibility of silage maturity kernels will be improved with gamma zein reduction.

Co-suppressed (i.e. low) 27 kD gamma zein corn produced as a top-cross onto Pioneer grain hybrid 3394 was compared with a control topcross and with the grain parent in a chicken feeding trial. A 21-d chick growth trial was performed with digestibility measurements, which demonstrated increased (by 2 percentage units) in vivo dry matter digestibility and increased energy conversion efficiency (by 2%) for the low gamma zein topcross. In addition, in vivo protein digestibility was improved by 9 percentage units (from 69 to 78%), representing a 13% increase. The increase in protein digestibility resulted in a 29% decrease in nitrogen excretion into the environment.

The same low gamma zein topcross was also compared with the control topcross in a pig in vivo digestion trial. Metabolizable Energy content of the low gamma zein topcross amounted to 3646 kcal/kg, 73 kcal (or 2%) higher than the control topcross. Protein digestibility was improved from 75.8 to 79.8% for the low gamma zein topcross. This represents a 5% improvement in protein digestibility, and a 15% reduction in nitrogen excretion into the environment.

Example 3

Suppression of 27 kD Gamma-Zein through Interruption of the 27 kD Gamma-Zein Gene by Transposon Tagging A maize line containing a Mu-insertion in the 27 kD gamma-zein gene was selected from the Pioneer TUSC collection using the TUSC process (Bensen et al. (1995) *Plant Cell* 7:75–84; Mena et al. (1996) *Science* 274:1537–1540; U.S. Pat. No. 5,962,764) with the 27 kD gamma-zein gene specific primers. Homozygous seed with the Mu-allele showed an absolute suppression of 27 kD gamma-zein protein. The trait has been stable in backcrosses to inbred lines. Again, seed are normal (vitreous) and have an unaltered test weight. The lysine content of the grain was increased 15–30% compared to wild-type grain. A maize line containing a Mu-insertion in the 27 kD gamma-zein gene was used.

Grain from progeny of this TUSC line has been tested in the in vitro digestibility assay with similar results as observed with the 27 kD gamma-zein gene co-suppressed lines (see Example 2). The trait is semi-dominant rather than recessive, that is the 27 kD gamma-zein level in endosperm shows a strong gene-dosage effect. For example, normal corn, pollinated with pollen from this 27 kD gamma-zein gene knock-out line shows at least 30% suppression of 27 kD gamma-zein protein in the heterozygous endosperm. Grain from these crosses showed a significant (6–10% after 4 hours) improvement in digestibility as demonstrated by the in vitro digestibility assay.

Example 4

Suppression of 27 kD Gamma-Zein by Over-Expression of High-Sulfur Proteins through Competition for Biosynthetically Available Pools of Sulfur Amino Acids Transgenic plants expressing the 18 kD delta-zein protein or the engineered high-lysine, high-sulfur protein hordothionin 12 (U.S. Pat. No. 5,990,389) in the endosperm showed an 80% decrease in gamma-zein protein levels due to limitations of free sulfur-amino acid pools. Seed from these events were tested essentially under the same conditions as seed from gamma-zein gene co-suppressing events (see Example 2) using the in vitro digestibility assay in both the presence and absence of disulfide reducing agents. The results obtained were similar to those described in the previous two Examples. The reduced levels of gamma-zein protein had a large positive impact on dry matter digestibility in the absence of DTT. Comparable results were also obtained using hemizygous seed from top-crossed elite inbreds and hybrids with hordothionin 12 corn as the male parent. Maize plants ectopically expressing 18 kD delta-zein protein or hordothionin 12 protein in corn endosperm were both produced using the top-cross technology. Grain from these plants showed the combined traits of improved amino acid composition and improved digestibility (energy availability). For procedures to determine amino acid composition see: Williams, A. P. 1994. Recent developments in amino acid analysis. In: *Amino Acids in Farm Animal Nutrition;* CAB International, Wallingford, U.K., pp.11–36

Example 5

Cloning of a Novel Maize 18 kD Alpha-globulin

An 18 kD alpha-globulin full-length CDNA (B73 allele) was cloned from a maize endosperm library (mid and late development). Based on EST numbers alpha-globulin transcripts are relatively rare (compared to other seed protein transcripts) and represent approximately 0.1% of the endosperm mRNA during mid development. Different maize inbred lines showed considerable allelism including several SNP's. The 18 kD alpha-globulin gene has been located on chromosome 6, bin 6.05.

The coding region of the B73 allele is 618 bp. The encoded 206 amino acid sequence of the pro-polypeptide contains a predicted N-terminal ER import signal peptide of 23 amino acids. Remarkable is the string of tryptophane (A) residues ("tryptophane box"), which has been also observed in puroindolins from wheat. Puroindolins in wheat have been associated with grain hardness. The 18 kD alpha-globulin of the present invention and the puroindolins are distantly evolutionary related and belong both to the 2S albumin gene superfamily.

SNP's and Alleles

Different corn inbred lines show considerable allelism. For example, sequence fragments isolated from B73 and Mo17 are shown below. The two alleles differ by mostly insertions '*' and a few SNP's (lower case bold). (See also SEQ ID NOS: 9 and 10).

```
18 kD alpha-globulin, B73 allele, partial

AATTCGCCCTTGTCATTCTGGATTTGCACGCGCACAGTACACATGCTGCGtCTTG

CACgTCGCGCCGACTCgCTtT*********AACCaTGGTAGCTAGTACTGGTCGCCGC

CGGAGAAGATGCTGCACTCCTGGGGCTCCGACAGCCGGCACATCATCGGCAAC

CCCGCGGCGTACTCCCGGGCCTTCGTAAGCCTCACGCGGCCGATCCTTGGCCC

GCCGCCGGTGGTGCCGGGACGACACGGTGGATACATCTGCcgcTGGccaCCCTg aCCgtagCCGTATCCCTCTCCTGGCCGGCTGCAGGGGTAGTAGTAGCCCCCCTG

TCCTCCTCCTCCTCCCTGCGGCGGCGGCTGCTGCTGCCGCCCCCATGGCCACC

AGCCTTTCTCCAGcGGCGGCATGGCCTCCTCGTAGCCCCTGACCATGCTCCGG

ATGGCGGCGCAGCGGCACTCGCGGCTCACGTCCTGGAGCTGCTGGCAGCACC

GCATCCGGAGCCCGGTGCCCCACCGGAACGGGCCAACGCGCCGCCGcCGCC

GCCGCCGGTTAGCTGCCGGTCGAGGAAAGGGCG 18 kD alpha-globulin, Mo17 allele, partial

AATTCGCCCTTGTCATTCTGGATTTGCACGCGCACAGTACACATGCTGCGCTT

GCACGTCGCGCCGACTCACTCTTTTTTTTTTAACCCTGGTAGCTAGTACTGGTCG

CCGCCGGAGAAGATGCTGCACTCCTGGGGCTCCGACAGCCGGCACATCATCGG

CAACCCCGCGGCGTACTCCCGGGCCTTCGTAAGCCTCACGCGGCCGATCCTTG

GCCC******GGTGGTGCCGGGACGACACGGTGGATACATCTGCGTTTGGTATCCC

TCTCCTGCCC***************GGCTGCAGGGGTAGTAGTAGCCCCCCTGTCCTC
```

-continued

```
CTCCTCCTCCCTGCGGCGGCGGCTGCTGCTGCCGCCCCCATGGCCACCAGCCT

TTCTCCAGAGGCGGCATGGCCTCCTCGTAGCCCCTGACCATGCTCCGGATGGC

GGCGCAGCGGCACTCGCGGCTCACGTCCTGGAGCTGCTGGCAGCACCGCATC

CGGAGCCCGGTGCCCCACCGGAACGGGCC*********GCCGACGCCGCCGCCGG

TTAGCTGCCGGTCGAGGAAAGGGCG
```

Example 6

Transgenic Expression of 18 kD Alpha-globulin in Maize

The cDNA encoding the maize 18 kD alpha-globulin was placed under the control of the strong endosperm specific gamma-zein promoter and introduced into maize plants by *Agrobacterium*-mediated transformation. Several transgenic events were identified that had increased levels alpha-globulin protein as demonstrated by SDS-PAGE and staining of gels with Coomassie blue. A prominent band was visible at a molecular weight corresponding to the 18 kD protein extracted from transgenic seed, but absent from protein extracted similarly from wild type seed. The seed of transformants and progeny overexpressing 18kD alpha-globulin is phenotypically normal (vitreous).

The identity of the polypeptide migrating at 18 kD in the polyacrylamide gel was confirmed by immune blotting using 18 kD alpha-globulin protein specific antibodies. In seed of transgenic plants, the 18 kD alpha-globulin protein accumulates to levels of between 2–5% of the SDS-sample buffer (60 mM Tris, pH 6.8, 100 mM DTT, 2% SDS) extractable seed protein. Seed expressing these amounts of omega zein protein contain 0.12% tryptophan per dry weight compared to No. 2 yellow corn having 0.06% tryptophan amounting to a 100% increase in tryptophan levels. Also, sulfur amino acid content was increased by about 80%. In vitro dry matter digestibility of corn overexpressing 18kD alpha-globulin was determined using the monogastric EDDM assay.

18 kD Alpha-globulin overexpression resulted in improved 4 hr EDDM by 10.6 percentage units. An overnight soak in 10 mM of the strong reducing agent dithio-threietol (DTT), known to maximize in vitro digestibility. Improved digestibility beyond that reached with 18 kb alpha-globulin overexpression (by 3.4 percentage units), indicated that the improvement in digestibility attainable with removing digestion-limiting disulfide bonds is partially additive to the improvement obtained with alpha-globulin overexpression. Similarly, improvements made by combining gamma zein co-suppression and 18 kD alpha globulin overexpression can be expected to be partially additive.

Example 7

Preparation of Maize 18 kD Alpha-globulin-Specific Antibodies

Standard methods for the production of antibodies were used such as those described in Harlow and Lane (1988) *Antibodies: A Laboratory Manual* (Cold Spring Harbor, N.Y.: Cold Spring Harbor Laboratory; incorporated herein in its entirety by reference. Specifically, antibodies for 18 kD alpha-globulin polypeptides were produced by injecting female New Zealand white rabbits (Bethyl Laboratory, Montgomery, Tex.) six times with homogenized polyacrylamide gel slices containing 100 micrograms of PAGE purified alpha-globulin polypeptide. The alpha-globulin polypeptide was purified by sub-cloning into a pET28 vector resulting in an insert encoding a His-tag fusion of the alpha-globulin polypeptide. The fusion protein was expressed in *E. coil* BL21(DE3) cells and purified from the lysate by Nickel chelation chromatography. The denatured purified fusion protein was used for immunization.

Animals were then bled at two week intervals. The antibodies were further purified by affinity-chromatography with Affigel 15 (BioRad)-immobilized antigen as described by Harlow and Lane (1988) *Antibodies: A Laboratory Manual*, Cold Spring Harbor, N.Y. The affinity column was prepared with purified 18 kD alpha-globulin protein essentially as recommended by BioRad RTM. Immune detection of antigens on PVDF blots was carried out following the protocol of Meyer et al. (1988) *J. Cell. Biol.* 107:163; incorporated herein in its entirety by reference, using the ECL kit from Amersham (Arlington Heights, Ill.).

Example 8

Cloning of a Maize 50 kD Legumin 1 Prolamin

A 50 kD legumin 1 nucleotide sequence was cloned from a maize endosperm cDNA library (mid and late development). Based on EST numbers 50 kD legumin 1 transcripts are relatively abundant (compared to other seed protein transcripts) and represent approximately 0.5% of the endosperm mRNA during mid development. The 50 kD legumin 1 DNA sequences isolated from different inbred lines showed a considerable level of polymorphism. The 50 kD legumin 1 gene has been mapped to chromosome 6, Bin 6.01.

Example 9

Preparation of Maize 50 kD Legumin 1-Specific Antibodies

Antibodies to this protein were prepared essentially as described for the 18 kD alpha-globulin polypeptide.

Example 10

Transgenic Expression of 50 kD Legumin 1 in Maize

Additional copies of the 50 kD legumin 1 cDNA under control of the strong endosperm specific gamma-zein promoter were introduced into transgenic corn plants. Several maize lines were identified that over-express the 50 kD legumin 1 protein. Over-expression was demonstrated by SDS-PAGE and staining of the gels with Coomassie blue. A prominent band was visible at 50 kD in protein extracted from transgenic seed but absent in protein from wild type seed. The identity of the polypeptide band was confirmed to be the 50 kD legumin 1 protein by immune blotting using the 50 kD legumin 1 protein specific antibodies. In the seed of transgenic maize plants over-expressing the 50 kD legumin 1 protein, this protein accumulates to levels of between 2–5% of the SDS-sample buffer (60 mM Tris, pH 6.8, 100 mM DTT, 2% SDS) extractable seed protein. The seed over-expressing the 50 kD legumin 1 protein showed a normal (vitreous) phenotype. In addition to overexpression of the 50 kD legumin 1, independent transformants were also obtained in which the legumin 1 gene was silenced as evidenced by reduced protein level using immune blotting. These events were also silenced for the 27 kD gamma zein, by apparent promoter-induced silencing. Finally, one event was obtained in which the 27 kD gamma zein was silenced, but the 50 KD legumin 1 clearly overexpressed as assessed by SDS-PAGE/Coomassie blue staining and immune blotting. Seed from all these events were phenotypically normal (vitreous)

Two segregating events, both silenced for 27 kD gamma zein, but only one overexpressing the corn legumin 1, were evaluated in the monogastric EDDM assay. 50 kD legumin 1 overexpression in low gamma zein background resulted in improved grain digestibility by about 3.2 percentage units.

These results imply not only that overexpression of corn 50 kD legumin1 improves digestibility, but that these improvements are additive to those obtained with gamma zein co-suppression.

Example 11

Agrobacterium-Mediated Transformation of Maize

For Agrobacterium-mediated transformation of maize, a nucleotide sequence encoding a protein of the present invention was operably linked to either the 27 kD gamma-zein promoter or the maize 19 kD alpha-zein (cZ19B1) promoter, and the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of Agrobacterium, where the bacteria are capable of transferring the nucleotide sequence of interest to at least one cell of at least one of the immature embryos (step 1: the infection step). In this step the immature embryos were immersed in an Agrobacterium suspension for the initiation of inoculation. The embryos were co-cultured for a time with the Agrobacterium (step 2: the co-cultivation step). The immature embryos were cultured on solid medium following the infection step. Following this co-cultivation period an optional "resting" step is contemplated. In this resting step, the embryos were incubated in the presence of at least one antibiotic known to inhibit the growth of Agrobacterium without the addition of a selective agent for plant transformants (step 3: resting step). The immature embryos were cultured on solid medium with antibiotic, but without a selecting agent, for elimination of Agrobacterium and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

Example 12

Agrobacterium-Mediated Transformation of Sorghum

For Agrobacterium-mediated transformation of sorghum the method of Cai et al. can be employed (U.S. patent application Ser. No. 09/056,418), the contents of which are hereby incorporated by reference). This method can be employed with a nucleotide sequence encoding any of the proteins of the present invention using the promoters described in Example 11 herein, or another suitable promoter.

Example 13

Transformation of Maize Embryos by Particle Bombardment

Immature maize embryos from greenhouse donor plants are bombarded with a plasmid containing the nucleotide sequence encoding a protein of the present invention operably linked to a selected promoter plus a plasmid containing the selectable marker gene PAT (Wohlleben et al. (1988) Gene 70:25–37) that confers resistance to the herbicide Bialaphos. Transformation is performed as follows.

Preparation of Target Tissue

The ears are surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the nucleotide sequence encoding a protein of the present invention operably linked to a promoter is made. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
10 µl (1 µg) DNA in Tris EDTA buffer (1 µg total)
100 µl 2.5 M $CaCl_2$
10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for the desired phenotypic trait.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-l $H_2O$ following adjustment to pH 5.8 with KOH); 2.0 g/l Gelrite (added after bringing to volume with D-l $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-l $H_2O$ following adjustment to pH 5.8 with KOH); 3.0 g/l Gelrite (added after bringing to volume with D-l $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-l $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-l $H_2O$ after adjusting to pH 5.6); 3.0 g/l Gelrite (added after bringing to volume with D-l $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-l $H_2O$), 0.1 g/l myo-inositol, and 40.0 g/l sucrose (brought to volume with polished D-l $H_2O$ after adjusting pH to 5.6); and 6 g/l bacto-agar (added after bringing to volume with polished D-l $H_2O$), sterilized and cooled to 60° C.

Example 16

Transformation of Rice Embryogenic Callus by Bombardment

Embryogenic callus cultures derived from the scutellum of germinating seeds serve as the source material for transformation experiments. This material is generated by germinating sterile rice seeds on a callus initiation media (MS salts, Nitsch and Nitsch vitamins, 1.0 mg/l 2,4-D and 10 M $AgNO_3$) in the dark at 27–28° C. Embryogenic callus proliferating from the scutellum of the embryos is then transferred to CM media (N6 salts, Nitsch and Nitsch vitamins, 1 mg/l 2,4-D, Chu et al., 1985, *Sci. Sinica* 18:659–668). Callus cultures are maintained on CM by routine sub-culture at two week intervals and used for transformation within 10 weeks of initiation.

Callus is prepared for transformation by subculturing 0.5–1.0 mm pieces approximately 1 mm apart, arranged in a circular area of about 4 cm in diameter, in the center of a circle of Whatman #541 paper placed on CM media. The plates with callus are incubated in the dark at 27–28 C for 3–5 days. Prior to bombardment, the filters with callus are transferred to CM supplemented with 0.25 M mannitol and 0.25 M sorbitol for 3 hr. in the dark. The petri dish lids are then left ajar for 20–45 minutes in a sterile hood to allow moisture on tissue to dissipate.

Circular plasmid DNA from two different plasmids one containing the selectable marker for rice transformation and one containing the nucleotide of the invention, are co-precipitated onto the surface of gold particles. To accomplish this, a total of 10 g of DNA at a 2:1 ratio of trait:selectable marker DNAs is added to a 50 l aliquot of gold particles resuspended at a concentration of 60 mg ml-$^1$. Calcium chloride (50 l of a 2.5 M solution) and spermidine (20 l of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 l of absolute ethanol and sonicated (bath sonicator) for one second to disperse the gold particles. The gold suspension is incubated at −70° C. for five minutes and sonicated (bath sonicator) if needed to disperse the particles. Six l of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28–29 inches Hg. The macrocarrier is accelerated with a helium shock wave using a rupture membrane that bursts when the He pressure in the shock tube reaches 1080–1100 psi. The tissue is placed approximately 8 cm from the stopping screen and the callus is bombarded two times. Five to seven plates of tissue are bombarded in this way with the DNA-coated gold particles. Following bombardment, the callus tissue is transferred to CM media without supplemental sorbitol or mannitol.

Within 3–5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/l 00 mg of callus. Callus clumps are broken into fragments of less than 2 mm diameter by repeated dispensing through a 10 ml pipet. Three ml aliquots of the callus suspension are plated onto fresh SM media and the plates incubated in the dark for 4 weeks at 27–28° C. After 4 weeks, transgenic callus events are identified, transferred to fresh SM plates and grown for an additional 2 weeks in the dark at 27–28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+ 50 ppm hyg B) and placed under cool white light (~40 $Em^{-2}s^{-1}$) with a 12 hr photoperiod at 25° C. and 30–40% humidity. After 24 weeks in the light, callus generally begins to organize, and form shoots. Shoots are removed from surrounding callus/media and gently transferred to RM3 media (1/2×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2–3 weeks, when sufficient root and shoot growth has occurred. Plants are grown using a 12 hr/12 hr light/dark cycle using ~30/18° C. day/night temperature regimen.

Example 17

Breeding Crosses Made with Transformed Low Gamma Zein Lines

A transgenic line that segregated for co-suppressed 4-coumarate ligase (4CL) was planted and the segregating progeny was either self-fertilized or pollinated with the transgenic low gamma zein line (CS27). Ground grain samples were subjected to a two-stage in vitro-mimicking small intestinal digestion followed by large-intestinal fermentation. The improvement in digestibility for low gamma zein corn in this two-stage assay, and the independent improvement obtained with 4CL co-suppression were additive as indicated by the absence of interaction.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
    (a) the nucleotide sequence set forth in SEQ ID NO: 3, and
    (b) a nucleotide sequence encoding the amino acid sequence set forth in SEQ ID NO: 4.

2. An isolated nucleic acid molecule comprising the nucleotide sequence set forth in SEQ ID NO:3.

3. An isolated nucleic acid molecule comprising a nucleotide sequence encoding the amino acid sequence set forth in SEQ ID NO: 4.

4. An expression cassette comprising a nucleic acid molecule of claim 1, wherein the nucleic acid is operably linked to a promoter that drives expression in a plant cell.

5. The expression cassette of claim 4, wherein the promoter is selected from the group consisting of seed-preferred, constitutive, chemically regulatable, tissue-preferred, and developmentally regulated promoters.

6. A transformed plant comprising in its genome at least one stably incorporated expression cassette comprising a nucleotide sequence operably linked to a promoter that drives expression in a plant cell, wherein the nucleotide sequence is selected from the group consisting of:
    (a) the nucleotide sequence set forth in SEQ ID NO: 3, and
    (b) a nucleotide sequence encoding the amino acid sequence set forth in SEQ ID NO: 4.

7. The plant of claim 6 wherein the plant is selected from the group consisting of maize, wheat, barley, rice, rye, oats, and sorghum.

8. Transformed seed of the plant of claim 6.

9. The transformed plant of claim 6 wherein the nucleotide sequence comprises SEQ ID NO:3.

10. The transformed plant of claim 6 wherein the nucleotide encodes the amino acid sequence set forth in SEQ ID NO:4.

11. A transformed plant cell comprising in its genome at least one stably incorporated expression cassette comprising a nucleotide sequence operably linked to a promoter that drives expression in a plant cell, the nucleotide sequence selected from the group consisting of:
    (a) the nucleotide sequence set forth in SEQ ID NO: 3, and
    (b) a nucleotide sequence encoding the amino acid sequence set forth in SEQ ID NO: 4.

* * * * *

UNITED STATES PATENT AND TRADEMARK OFFICE
CERTIFICATE OF CORRECTION

PATENT NO. : 6,858,778 B1
DATED : February 22, 2005
INVENTOR(S) : Rudolf Jung et al.

It is certified that error appears in the above-identified patent and that said Letters Patent is hereby corrected as shown below:

Column 57,
Lines 46-49, should read as follows:
-- The expression cassette of claim 4, wherein the promoter is selected from the group consisting of seed-preferred, constitutive, chemically regulated, tissue-preferred, and developmentally regulated promoters. --

Column 58,
Lines 41-43, should read as follows:
-- The transformed plant of claim 6 wherein the nucleotide sequence encodes the amino acid sequence set forth in SEQ ID NO:4 --

Signed and Sealed this

Seventeenth Day of May, 2005

JON W. DUDAS
*Director of the United States Patent and Trademark Office*